United States Patent
Fukuoka et al.

(10) Patent No.: US 8,883,759 B2
(45) Date of Patent: Nov. 11, 2014

(54) ANTI-TUMOR EFFECT POTENTIATOR

(75) Inventors: Masayoshi Fukuoka, Tsukuba (JP); Tatsushi Yokogawa, Tsukuba (JP); Seiji Miyahara, Tsukuba (JP); Hitoshi Miyakoshi, Tsukuba (JP); Wakako Yano, Tsukuba (JP); Junko Taguchi, Tsukuba (JP); Yayoi Takao, Chiyoda (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 251 days.

(21) Appl. No.: 13/509,102

(22) PCT Filed: Nov. 29, 2010

(86) PCT No.: PCT/JP2010/071280
§ 371 (c)(1),
(2), (4) Date: May 10, 2012

(87) PCT Pub. No.: WO2011/065541
PCT Pub. Date: Jun. 3, 2011

(65) Prior Publication Data
US 2012/0225838 A1  Sep. 6, 2012

(30) Foreign Application Priority Data
Nov. 30, 2009  (JP) ................ 2009-272738

(51) Int. Cl.
*A61K 31/513* (2006.01)
*A61K 31/7072* (2006.01)
*A61K 31/519* (2006.01)
*C07D 239/54* (2006.01)
*A61P 35/00* (2006.01)
*A61K 45/06* (2006.01)
*C07D 405/12* (2006.01)

(52) U.S. Cl.
CPC ............ *C07D 239/54* (2013.01); *A61K 31/513* (2013.01); *A61K 31/7072* (2013.01); *A61K 45/06* (2013.01); *A61K 31/519* (2013.01); *C07D 405/12* (2013.01)
USPC ............................. 514/50; 514/274; 544/312

(58) Field of Classification Search
USPC .................... 514/50, 274; 544/312
See application file for complete search history.

(56) References Cited

U.S. PATENT DOCUMENTS

| 8,530,490 B2 * | 9/2013 | Fukuoka et al. ............ 514/274 |
| 2008/0300216 A1 | 12/2008 | Gilbert et al. |
| 2011/0082163 A1 | 4/2011 | Fukuoka et al. |

FOREIGN PATENT DOCUMENTS

| EP | 1939186 | 7/2008 |
| JP | 58 39672 | 3/1983 |
| JP | 9 286786 | 11/1997 |
| WO | 2005 065689 | 7/2005 |
| WO | 2009 147843 | 12/2009 |

OTHER PUBLICATIONS

The Merck Manual 1992, pp. 1263, 1266-69, 1277-80 and 1285.*
Kawahara et al, J. Clin. Pathol. 2009, 62, 364-69, published online Dec. 3, 2008.*
Trisha Gura , Science, Nov. 1997, pp. 1041-1042.*
Huang, Z. et al., "A novel kind of antitumour drugs using sulfonamide as parent compound", Eur. J. Med. Chem., vol. 36, pp. 863-872. (2001).
Kawahara, A. et al., "Higher expression of deoxyuridine triphosphatase (dUTPase) may predict the metastasis potential of colorectal cancer", J Clin Pathol, vol. 62, pp. 364-369. (2009).
Fleischmann, J. et al., "Expression of deoxyuridine triphosphatase (dUTPase) in colorectal tumors", Int. J. Cancer (Pred. Oncol.), vol. 84, pp. 614-617. (1999).
Ladner, R.D. et al., "dUTP Nucleotidohydrolase Isoform Expression in Normal and Neoplastic Tissues: Association with Survival and Response to 5-Fluorouracil in Colorectal Cancer", Cancer Res, vol. 60, pp. 3493-3503. (2000).
Koehler, S.E. et al., "Small Interfering RNA-Mediated Suppression of dUTPase Sensitizes Cancer Cell Lines to Thymidylate Synthase Inhibition", Molecular Pharmacology, vol. 66, pp. 620-626. (2004).
International Search Report issued on Dec. 28, 2010 in PCT/JP10/071280 filed on Nov. 29, 2010.

* cited by examiner

*Primary Examiner* — Ganapathy Krishnan
(74) *Attorney, Agent, or Firm* — Oblon, Spivak, McClelland, Maier & Neustadt, L.L.P.

(57) ABSTRACT

There is provided an agent for potentiating the effects of an anti-tumor agent.
An anti-tumor effect potentiator containing, as an active ingredient, a uracil compound represented by the following formula (I) or a pharmaceutically acceptable salt thereof:

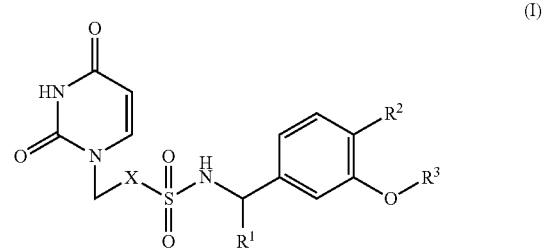

(I)

wherein X represents a $C_{1-5}$ alkylene group and one of methylene groups constituting the alkylene group is optionally substituted with an oxygen atom;
$R^1$ represents a hydrogen atom or a $C_{1-6}$ alkyl group; $R^2$ represents a hydrogen atom or a halogen atom; and $R^3$ represents a $C_{1-6}$ alkyl group, a $C_{2-6}$ alkenyl group, a $C_{3-6}$ cycloalkyl group, a ($C_{3-6}$ cycloalkyl) $C_{1-6}$ alkyl group, a halogeno-$C_{1-6}$ alkyl group or a saturated heterocyclic group.

12 Claims, 10 Drawing Sheets

ANTI-TUMOR EFFECT POTENTIATOR

FIELD OF THE INVENTION

The present invention relates to an anti-tumor effect potentiator for an anti-tumor agent, and an anti-tumor drug containing the same.

BACKGROUND OF THE INVENTION

Deoxyuridine triphosphatase (hereinafter referred to as dUTPase (EC3.6.1.23) at times) is a preventive DNA repair enzyme. This enzyme specifically recognizes only deoxyuridine triphosphate, distinguishing from other triphosphates of natural nucleic acids, and hydrolyses the deoxyuridine triphosphate to deoxyuridine monophosphate and pyrophosphoric acid. dUTPase is known to be an essential enzyme for the survival of both prokaryotic and eukaryotic cells.

In malignant tumors, it is suggested that malignancy is associated with high expression level of dUTPase (Non Patent document 1 and 2). It has also been reported that a tumor in which expression of the enzyme has been accelerated shows resistance to chemotherapy (Non Patent document 3). Moreover, potentiation of anti-tumor effect of a thymidylate synthase inhibitor (hereinafter referred to as a TS inhibitor) was observed when the expression level of dUTPase is decreased using siRNA in cultured cancer cells (Non Patent document 4). These findings suggest that human dUTPase inhibitors could be useful chemical sensitizers of anti-tumor agents.

PRIOR ART DOCUMENTS NON-PATENT DOCUMENTS

[Non Patent document 1]
J Clin Pathol. 2009 April; 62(4): 364-9
[Non Patent document 2]
Int J Cancer. 1999 Dec. 22; 84(6): 614-7
[Non Patent document 3]
Cancer Res. 2000 Jul. 1; 60(13): 3493-503
[Non Patent document 4] Mol. Pharmacol. 2004 September; 66(3): 620-6

SUMMARY OF THE INVENTION

Problem to be Solved

However, there is no report that a small molecule inhibitor of human dUTPase effect actually exhibits anti-tumor effect potentiating effect.

An object of the present invention is to provide an anti-tumor effect potentiator, for an anti-tumor agent, and an anti-tumor drug containing the same.

Means for Solving the Problem

As a result of intensive studies directed towards achieving the aforementioned object, the present inventors have found that a uracil compound having a sulfonamide structure at N-1 position of the uracil ring, represented by a formula (I) below, or a salt thereof shows potent human dUTPase inhibitory effect. The inventors have conducted further studies, and as a result, they have found that the aforementioned uracil compound or a salt thereof shows excellent enhancing activity for the efficacy of an anti-tumor agent (in particular, an antimetabolite), thereby completing the present invention.

The present invention provides an anti-tumor effect potentiator for an anti-tumor agent containing, as an active ingredient, a uracil compound represented by the following formula (I) or a pharmaceutically acceptable salt thereof:

[Formula 1]

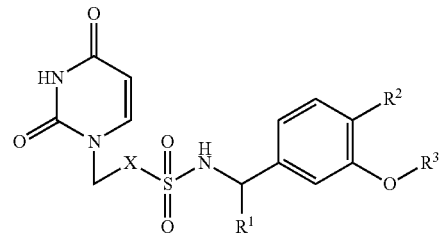

(I)

wherein X represents a $C_{1-5}$ alkylene group and one of methylene groups constituting the alkylene group is optionally substituted with an oxygen atom;
$R^1$ represents a hydrogen atom or a $C_{1-6}$ alkyl group; $R^2$ represents a hydrogen atom or a halogen atom; and $R^3$ represents a $C_{1-6}$ alkyl group, a $C_{2-6}$ alkenyl group, a $C_{3-6}$ cycloalkyl group, a ($C_{3-6}$ cycloalkyl) $C_{1-6}$ alkyl group, a halogeno-$C_{1-6}$ alkyl group or a saturated heterocyclic group.

In addition, the present invention provides an anti-tumor drug comprising combination of the uracil compound represented by the above formula (I) or a pharmaceutically acceptable salt thereof, and an anti-tumor agent.

Moreover, the present invention provides the uracil compound represented by the above formula (I) or a pharmaceutically acceptable salt thereof for use in potentiation of anti-tumor effects.

Furthermore, the present invention provides a combination of the compound represented by the above formula (I) or a pharmaceutically acceptable salt thereof and an anti-tumor agent for use in treating tumors.

Further, the present invention provides a method for potentiating anti-tumor effects, which includes administration of an effective amount of the compound represented by the above formula (I) or a pharmaceutically acceptable salt thereof.

Further, the present invention provides a method for treating tumors, which includes administration of a combination of the compound represented by the above formula (I) or a pharmaceutically acceptable salt thereof and an anti-tumor agent.

Still further, the present invention provides use of the compound represented by the above formula (I) or a pharmaceutically acceptable salt thereof for the production of an anti-tumor effect potentiator.

Still further, the present invention provides use of a combination of the compound represented by the above formula (I) or a pharmaceutically acceptable salt thereof and an anti-tumor agent for the production of an anti-tumor agent.

Effects of the Invention

The novel uracil compound of the present invention or a pharmaceutically acceptable salt thereof is useful as an anti-tumor effect potentiator for an anti-tumor agent (in particular, an antimetabolite), and as an anti-tumor drug containing the same.

DETAILED DESCRIPTION OF THE INVENTION

Figure 1:
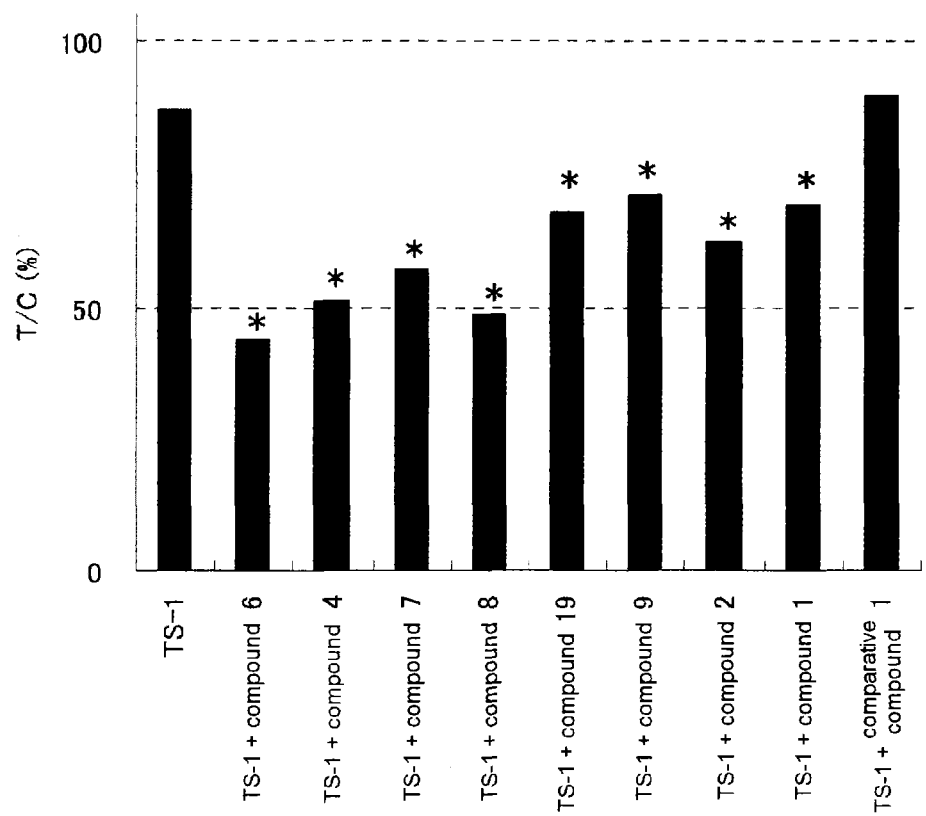
FIG. 1 is a diagram showing anti-tumor effect potentiating effect on TS-1.

In the formula (I), the "$C_{1-5}$ alkylene group" represented by X indicates a linear or branched alkylene group having 1 to 5 carbon atoms. Specific examples include a methylene group, an ethylene group, a trimethylene group, a tetramethylene group, a pentamethylene group, a propylene group, a butylene group, a dimethyltrimethylene group, and an ethyltrimethylene group. An example of the $C_{1-5}$ alkylene group, wherein one of methylene groups constituting the alkylene group is substituted with an oxygen atom, is an —O—$C_{1-4}$ alkylene group.

X is preferably an ethylene group or —O—CH$_2$CH$_2$CH$_2$—.

In the formula (I), the "$C_{1-6}$ alkyl group" represented by $R^1$ indicates a linear or branched hydrocarbon group having 1 to 6 carbon atoms. Specific examples include a methyl group, an ethyl group, an n-propyl group, an isopropyl group, an n-butyl group, a sec-butyl group, a tert-butyl group, an n-pentyl group, and an n-hexyl group. A $C_{1-3}$ alkyl group is preferable, and a methyl group and an ethyl group are more preferable.

In the formula (I), examples of the "halogen atom" represented by $R^2$ include a fluorine atom, a chlorine atom, a bromine atom, and an iodine atom. Of these, a fluorine atom is preferable.

In the formula (I), the "$C_{1-6}$ alkyl group" represented by $R^3$ includes the same groups as those described for 12$^1$ above. An isobutyl group and a 2-methylbutyl group are preferable.

In the formula (I), the "$C_{2-6}$ alkenyl group" represented by $R^3$ indicates a hydrocarbon group having 2 to 6 carbon atoms, which contains a carbon-carbon double bond. Examples thereof include a vinyl group, an allyl group, a methylvinyl group, a propenyl group, a butenyl group, a pentenyl group, and a hexenyl group. Of these, an allyl group is preferable.

In the formula (I), examples of the "$C_{3-6}$ cycloalkyl group" represented by $R^3$ include a cyclopropyl group, a cyclobutyl group, a cyclopentyl group, and a cyclohexyl group. Of these, a cyclopentyl group is preferable.

In the formula (I), the "($C_{3-6}$ cycloalkyl) $C_{1-6}$ alkyl group" represented by $R^3$ indicates an alkyl group having 1 to 6 carbon atoms, which has the above described cycloalkyl group. A cyclopropylmethyl group is preferable.

In the formula (I), the "halogeno-$C_{1-6}$ alkyl group" represented by $R^3$ indicates an alkyl group having 1 to 6 carbon atoms, which has the above described halogen atom. A 2,2-difluoroethyl group and a 2,2,2-trifluoroethyl group are preferable.

In the formula (I), the "saturated heterocyclic group" represented by $R^3$ preferably indicates a monocyclic or bicyclic saturated heterocyclic group preferably having any one or two atoms selected from oxygen, nitrogen, and sulfur atom(s). Examples thereof include a pyrrolidinyl group, a piperidinyl group, a piperazinyl group, a hexamethyleneimino group, a morpholino group, a thiomorpholino group, a homopiperidinyl group, a tetrahydrofuryl group, and a tetrahydropyryl group. Of these, a tetrahydrofuryl group and a tetrahydropyryl group are preferable.

The group represented by $R^3$ is preferably an isobutyl group, a 2-methylbutyl group, an allyl group, a cyclopentyl group, a cyclopropylmethyl group, a 2,2-difluoroethyl group, a 2,2,2-trifluoroethyl group, a tetrahydrofuryl group, or a tetrahydropyryl group.

It is more preferable that, in the formula (I), X represents an ethylene group or an —O—$C_{1-4}$ alkylene group; $R^1$ represents a hydrogen atom or a $C_{1-3}$ alkyl group; $R^2$ represents a hydrogen atom or a fluorine atom; and $R^3$ represents a $C_{1-6}$ alkyl group, a $C_{2-6}$ alkenyl group, a $C_{3-6}$ cycloalkyl group, a ($C_{3-6}$ cycloalkyl) $C_{1-6}$ alkyl group, a halogeno-$C_{1-6}$ alkyl group or a saturated heterocyclic group.

In addition, it is further preferable that, in the formula (I), X represents an ethylene group or an —O—$C_{1-4}$ alkylene group; $R^1$ represents a hydrogen atom or a $C_{1-3}$ alkyl group; $R^2$ represents a hydrogen atom or a fluorine atom; and $R^3$ represents a $C_{1-6}$ alkyl group, a $C_{2-6}$ alkenyl group, a ($C_{3-6}$ cycloalkyl) $C_{1-6}$ alkyl group, a halogeno-$C_{1-6}$ alkyl group, or a tetrahydrofuryl or tetrahydropyryl group.

Moreover, it is particularly preferable that, in the formula (I), X represents an ethylene group or —O—CH$_2$CH$_2$CH$_2$—; $R^1$ represents a hydrogen atom, a methyl group or an ethyl group; $R^2$ represents a hydrogen atom or a fluorine atom; and $R^3$ represents an isobutyl group, a 2-methylbutyl group, an allyl group, a cyclopentyl group, a cyclopropylmethyl group, a 2,2-difluoroethyl group, a 2,2,2-trifluoroethyl group, a tetrahydrofuryl group or a tetrahydropyryl group.

Examples of a pharmaceutically acceptable salt of the compound represented by the formula (I) include: acid addition salts with inorganic acids such as hydrochloric acid, hydrobromic acid, hydroiodic acid, sulfuric acid, nitric acid or phosphoric acid, or with organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, paratoluenesulfonic acid or glutamic acid; salts with inorganic bases such as sodium, potassium, magnesium, calcium or aluminum, or with organic bases such as methylamine, ethylamine, meglumine or ethanolamine, or with basic amino acids such as lysine, arginine or ornithine; and ammonium salts. Moreover, the compound of the present invention includes an optical isomer and hydrate(s).

The uracil compound of the present invention can be produced according to the following reaction steps.

[Step A]

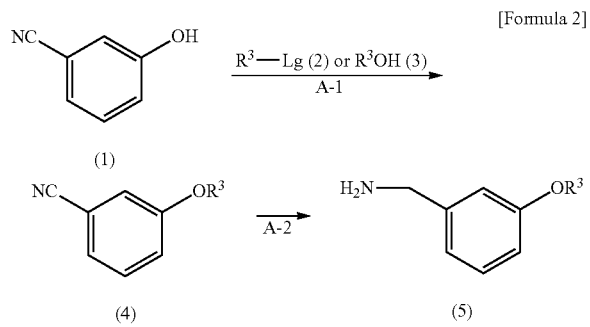

[Formula 2]

wherein $R^3$ is as defined above; and Lg represents a leaving group such as a halogen atom, a methanesulfonyloxy group, a p-toluenesulfonyloxy group or a trifluoromethanesulfonyloxy group.

[A-1]

(a) In this step, a commercially available 3-cyanophenol (1) can be reacted with an alkyl halide, alkyl mesylate, alkyl tosylate, alkyl trifluoromethanesulfonate represented by the general formula (2) in the presence of a base to produce a compound represented by the general formula (4).

Any reaction solvent that does not affect the reaction can be used without limitations. Examples thereof include diethyl ether, tetrahydrofuran (hereinafter, referred to as THF), dioxane, acetone, dimethoxyethane, acetonitrile, N,N-dimethylformamide (hereinafter, referred to as DMF), N,N-dimethylacetamide (hereinafter, referred to as DMA), and dimethyl sulfoxide (hereinafter, referred to as DMSO). Of these, DMF is preferable.

Examples of a base used herein include: inorganic bases such as sodium bicarbonate, sodium carbonate, potassium carbonate, cesium carbonate, sodium hydride, potassium hydride, sodium hydroxide or potassium hydroxide; and organic amines such as trimethylamine, triethylamine, tripropylamine, diisopropylethylamine, N-methylmorpholine, pyridine, lutidine or collidine. Of these, potassium carbonate is preferable. The equivalent number thereof is 0.8 to 10 equivalents, and preferably 1.0 to 5.0 equivalents.

The equivalent number of the compound of the general formula (2) is 0.8 to 10 equivalents, and preferably 1.0 to 5.0 equivalents. The reaction temperature is 20 to 150° C., and preferably 50 to 130° C. The reaction time is 0.5 to 24 hours, and preferably 1.0 to 12 hours.

(b) In this step, the commercially available 3-cyanophenol (1) and an alcohol represented by the general formula (3) can be condensed by Mitsunobu reaction to produce the compound represented by the general formula (4).

Any reaction solvent that does not affect the reaction can be used without limitations. Examples thereof include dichloromethane, 1,2-dichloroethane (hereinafter, referred to as DCE), benzene, xylene, toluene, ethyl acetate, propyl acetate, butyl acetate, diethyl ether, THF, dioxane, acetone, dimethoxyethane, acetonitrile, and DMF. Of these, THF is preferable.

Any reagent that can usually be used in the Mitsunobu reaction can be used in this reaction without limitations. Examples thereof include combinations of di-lower alkyl azodicarboxylate (e.g., diethyl azodicarboxylate (hereinafter, referred to as DEAD) or diisopropyl azodicarboxylate (hereinafter, referred to as DIAD)), or an azo compound (e.g., azodicarbonyl such as 1,1-(azodicarbonyl)dipiperidine) with triarylphosphine (e.g., triphenylphosphine) or tri-lower alkylphosphine (e.g., tri-n-butylphosphine). A combination of DEAD with triphenylphosphine is preferable.

The equivalent numbers of the alcohol of the general formula (3), the di-lower alkyl azodicarboxylate and the triarylphosphine are respectively 0.8 to 5.0 equivalents, and preferably 1.0 to 2.0 equivalents. The reaction temperature is −20° C. to 120° C., and preferably 0 to 60° C. The reaction time is 0.1 to 24 hours, and preferably 0.2 to 6.0 hours.

[A-2]

In this step, the cyano compound represented by the general formula (4) can be reacted with a generally known reducing agent to produce a compound represented by the general formula (5).

A reaction solvent differs depending on the type of reduction reaction. Examples thereof include methanol, ethanol, 1-propanol, 2-propanol, tert-butyl alcohol, dimethoxyethane, diethylene glycol dimethyl ether, diisopropyl ether, diethyl ether, THF, and dioxane. Of these, THF is preferable.

Examples of the reducing agent used herein include: metal hydrides such as lithium aluminum hydride (hereinafter, referred to as LAH), lithium diethoxyaluminum hydride, lithium triethoxyaluminum hydride, lithium tri-tert-butoxyaluminum hydride, magnesium aluminum hydride, aluminum hydride with magnesium chloride, sodium aluminum hydride, sodium triethoxyaluminum hydride or sodium bis (2-methoxyethoxy)aluminum hydride; and catalysts used for hydrogenation, such as palladium/carbon, palladium hydroxide or platinum. Of these, LAH is preferable. The equivalent number thereof is 0.5 to 5.0 equivalents, and preferably 0.8 to 2.0 equivalents. The reaction temperature is 0° C. to 100° C., and preferably 20 to 60° C. The reaction time is 0.1 to 24 hours, and preferably 0.2 to 6.0 hours.

[Step B]

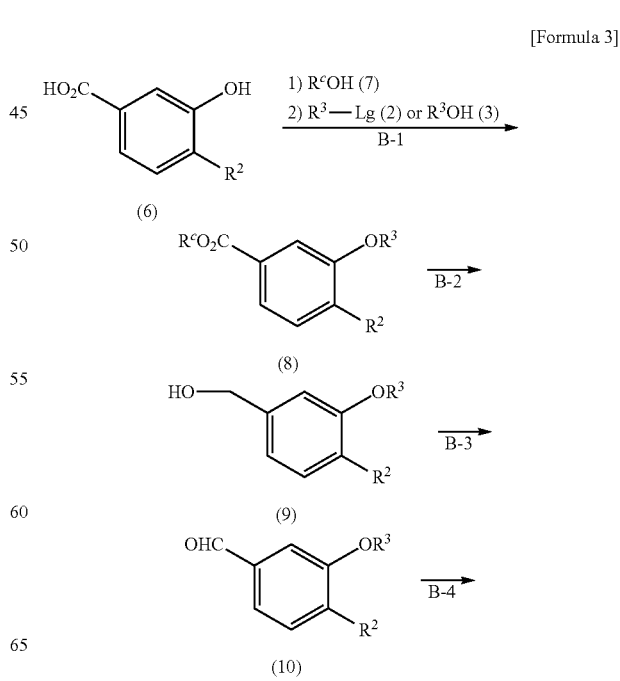

[Formula 3]

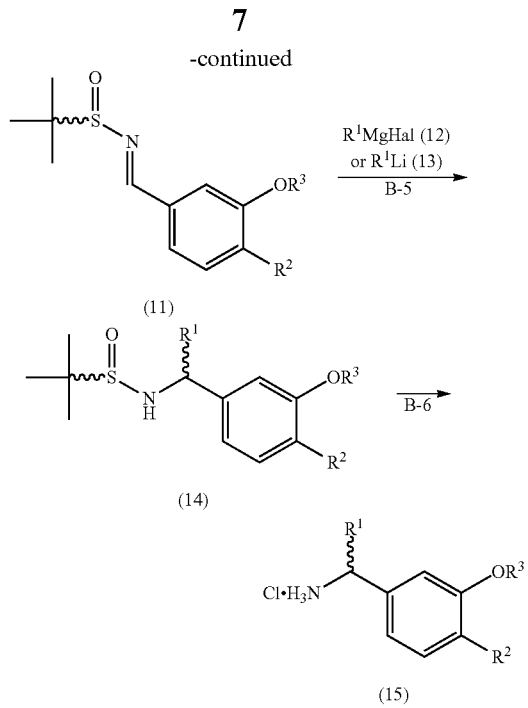

wherein $R^1$, $R^2$, $R^3$ and Lg are as defined above; re represents a $C_{1-6}$ alkyl group; and Hal represents a halogen atom.

[B-1]

In this step, the carboxyl group of an easily available compound (6) is esterified with an alcohol compound (7) by a usually known method, and the resultant compound can then be reacted in the same way as in the step [A-1] to produce a compound represented by the general formula (8).

[B-2]

In this step, the compound represented by the general formula (8) can be reacted with a generally known reducing agent to produce a compound represented by the general formula (9).

Any reaction solvent that does not affect the reaction can be used without limitations. Examples thereof include diethyl ether, diisopropyl ether, THF, and dioxane. Of these, THF is preferable.

Examples of a reducing agent used herein include LAH, lithium diethoxyaluminum hydride, lithium triethoxyaluminum hydride, lithium tri-tert-butoxyaluminum hydride, magnesium aluminum hydride, aluminum hydride with magnesium chloride, sodium aluminum hydride, sodium triethoxyaluminum hydride, sodium bis(2-methoxyethoxy) aluminum hydride, diisobutylaluminum hydride (hereinafter, referred to as DIBAL), and lithium borohydride. Of these, lithium borohydride is preferable. The equivalent number thereof is 0.8 to 10 equivalents, and preferably 1.0 to 5.0 equivalents. The reaction temperature is 0° C. to the boiling point of the solvent, and preferably the boiling point of the solvent. The reaction time is 0.1 to 24 hours, and preferably 0.5 to 12 hours.

[B-3]

In this step, the compound represented by the general formula (9) can be reacted with a generally known oxidizing agent to produce an aldehyde compound represented by the general formula (10).

Any reaction solvent that does not affect the reaction can be used without limitations. Examples thereof include dichloromethane, chloroform, carbon tetrachloride, DCE, chlorobenzene, toluene, and xylene. Of these, dichloromethane is preferable.

Examples of the oxidizing agent used herein include: a complex reagent of chromic anhydride, pyridine and acetic anhydride; chromium-based oxidizing agents such as pyridinium chlorochromate or pyridinium dichromate; hypervalent iodine oxidizing agents such as a Dess-Martin reagent; DMSO-based oxidizing agents such as DMSO used in combination with acetic anhydride, oxalyl chloride, dicyclohexylcarbodiimide (hereinafter, referred to as DCC) or 1-ethyl-3-(3-dimethylaminopropyl)carbodiimide hydrochloride (hereinafter, referred to as EDC-HCl); manganese(IV) oxide; and 2,2,6,6-tetramethylpiperidin-1-oxyl radicals. Of these, manganese(IV) oxide is preferable. The equivalent number thereof is 0.8 to 30 equivalents, and preferably 1.0 to 20 equivalents. The reaction temperature is −20 to 150° C., and preferably 0 to 100° C. The reaction time is 0.1 to 24 hours, and preferably 0.5 to 12 hours.

When $R^2$ is a hydrogen atom, commercially available 3-hydroxybenzaldehyde can be reacted as a starting material in the same way as in the step [A-1] to produce the compound represented by the general formula (10). Furthermore, the nitrile compound represented by the general formula (4) can also be reduced by a generally known reduction reaction, for example, a DIBAL reduction method to produce the compound represented by the general formula (10).

[B-4]

In this step, the compound represented by the general formula (10) or commercially available aldehyde can be reacted with commercially available 2-methyl-2-propanesulfinamide under acidic conditions to produce a compound represented by the above general formula (11).

Any reaction solvent that does not affect the reaction can be used without limitations. Examples thereof include diethyl ether, diisopropyl ether, THF, dioxane, dichloromethane, chloroform, carbon tetrachloride, toluene, and xylene. Of these, toluene is preferable.

Examples of an acid used herein include hydrochloric acid, sulfuric acid, p-toluenesulfonic acid, and Lewis acid (e.g., titanium tetraisopropoxide or titanium tetraethoxide). Of these, titanium tetraisopropoxide is preferable. The equivalent numbers of the 2-methyl-2-propanesulfinamide and the titanium tetraisopropoxide are respectively 0.8 to 10 equivalents, and preferably 1.0 to 3.0 equivalents. The reaction temperature is 20 to 150° C., and preferably 50 to 120° C. The reaction time is 0.1 to 24 hours, and preferably 0.5 to 6.0 hours.

[B-5]

In this step, the compound represented by the general formula (11) can be reacted with a Grignard reagent (12) represented by $R^1$MgHal or an organic lithium reagent (13) represented by $R^1$Li to produce a compound represented by the general formula (14) diastereoselectively.

Any reaction solvent that does not affect the reaction can be used without limitations. Examples thereof include diethyl ether, diisopropyl ether, tert-butyl methyl ether, cyclopentyl methyl ether, THF, dimethoxyethane, dioxane, dichloromethane, chloroform, carbon tetrachloride, toluene, and xylene. The equivalent amount of the Grignard reagent or the organic lithium reagent is 0.8 to 20 equivalents, and preferably 1.0 to 10 equivalents. The reaction temperature is −100° C. to 100° C., and preferably −78° C. to 50° C. The reaction time is 0.1 to 24 hours, and preferably 0.5 to 12 hours.

[B-6]

In this step, the compound represented by the general formula (14) can be treated with an acid to produce a compound represented by the general formula (15).

Any solvent that does not affect the reaction can be used without limitations. Examples thereof include: alcohols such as methanol, ethanol, 1-propanol, 2-propanol, 1-butanol or 2-butanol; dioxane; and ethyl acetate. Of these, methanol is preferable.

Examples of the acid used herein include hydrochloric acid, sulfuric acid, and phosphoric acid. Of these, hydrochloric acid is preferable. The equivalent number thereof is 0.1 to 10 equivalents, and preferably 1.0 to 2.0 equivalents. The reaction temperature is −20° C. to 100° C., and preferably 0 to 50° C. The reaction time is 0.01 to 24 hours, and preferably 0.1 to 1.0 hour.

In addition, when $R^1$ is a hydrogen atom and $R^2$ is a fluorine atom, the compound represented by the general formula (9) can be azidated by a generally known method and then treated with a generally known reducing agent (e.g. LAH) to produce the compound represented by the general formula (15). Furthermore, in a case where the compound represented by the general formula (15) can be obtained as a racemate, the compound represented by the general formula (10) can be converted to an alcohol compound by the same method as in the step [B-5], the alcohol compound can be subsequently azidated by a generally known method, and the resulting azide compound can then be reduced by a generally known method to produce the compound represented by the general formula (15).

[Step C]

[Formula 4]

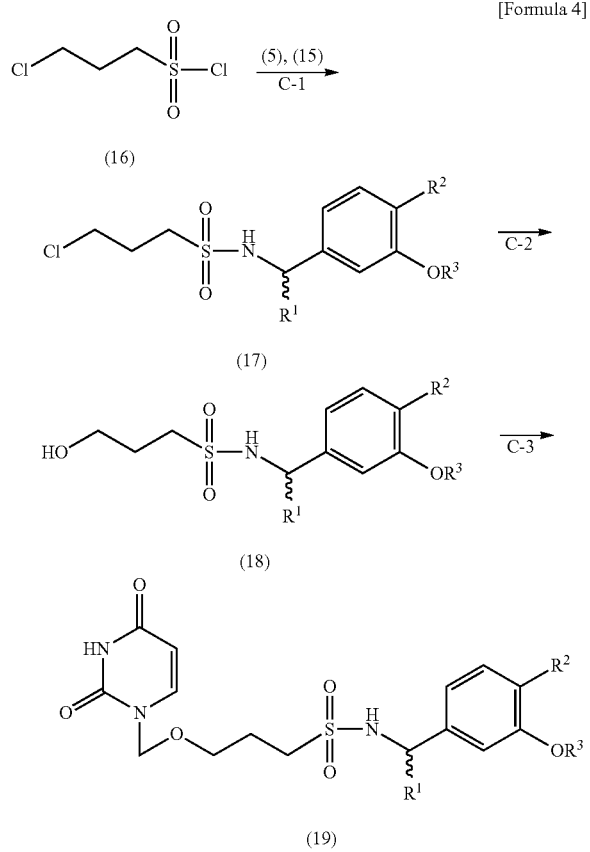

wherein $R^1$, $R^2$ and $R^3$ are as defined above.

[C-1]

In this step, an easily available 3-chloro propane sulfonyl chloride (16) can be reacted with any amine represented by the general formula (5) or (15) in the presence of a base to produce a compound represented by the general formula (17).

Any reaction solvent that does not affect the reaction can be used without limitations. Examples thereof include acetone, THF, diethyl ether, diisopropyl ether, dioxane, dichloromethane, chloroform, carbon tetrachloride, DMF, DMA, and acetonitrile. Of these, dichloromethane is preferable.

Examples of the base used herein include: inorganic bases such as sodium bicarbonate, sodium carbonate or potassium carbonate; and organic amines such as trimethylamine, triethylamine, tripropylamine, diisopropylethylamine, N-methyl morpholine, pyridine, lutidine, or collidine. Of these, triethylamine is preferable. The equivalent numbers of the base and the amine are respectively 0.5 to 10 equivalents, and preferably 0.7 to 5.0 equivalents. The reaction temperature is −20° C. to 100° C., and preferably 0 to 50° C. The reaction time is 0.1 to 24 hours, and preferably 0.2 to 6.0 hours.

[C-2]

In the present step, the chloro compound represented by the general formula (17) can be acetoxylated through reaction with an acetoxylating reagent by a general method and then deacetylated by a general method to produce an alcohol compound represented by the general formula (18).

[C-3]

In this step, the compound represented by the general formula (18) can be methoxymethylated (MOM-induced) by a general method, subsequently treated with a Lewis acid, and then reacted with a 2,4-bis(trimethylsilyloxy)pyrimidine obtained according to the method described in the document (Nucleosides & Nucleotides, 4, 565-585 (1985)) in the presence of iodine to produce a compound represented by the general formula (19).

Any reaction solvent that does not affect the reaction can be used in the Lewis acid treatment without limitations. Examples thereof include dichloromethane, chloroform, carbon tetrachloride, DCE, toluene, and xylene. Of these, dichloromethane is preferable. Examples of the Lewis acid include boron trichloride (hereinafter, referred to as $BCl_3$), boron trifluoride, and boron tribromide. Of these, $BCl_3$ is preferable. The equivalent number thereof is 0.01 to 10 equivalents, and preferably 0.2 to 0.5 equivalents. The reaction temperature is −20 to 100° C., and preferably 0 to 50° C. The reaction time is 0.1 to 24 hours, and preferably 0.5 to 5.0 hours.

Any reaction solvent that does not affect the reaction can be used in the reaction with the 2,4-bis(trimethylsilyloxy)pyrimidine without limitations. Examples thereof include dichloromethane, chloroform, carbon tetrachloride, DCE, toluene, and xylene. Of these, DCE or toluene is preferable. The equivalent number of the 2,4-bis(trimethylsilyloxy)pyrimidine is 0.8 to 10 equivalents, and preferably 0.9 to 5.0 equivalents. The equivalent number of iodine is 0.001 to 1.0 equivalent, and preferably 0.05 to 0.5 equivalents. The reaction temperature is 20 to 150° C., and preferably 50 to 100° C. The reaction time is 0.1 to 120 hours, and preferably 0.5 to 100 hours.

[Step D]

[Formula 5]

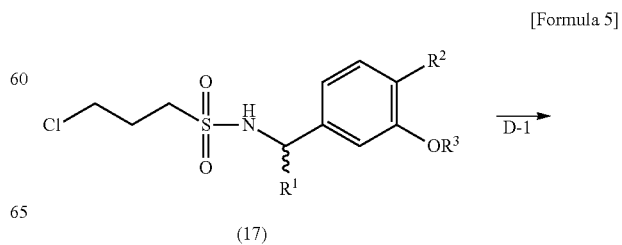

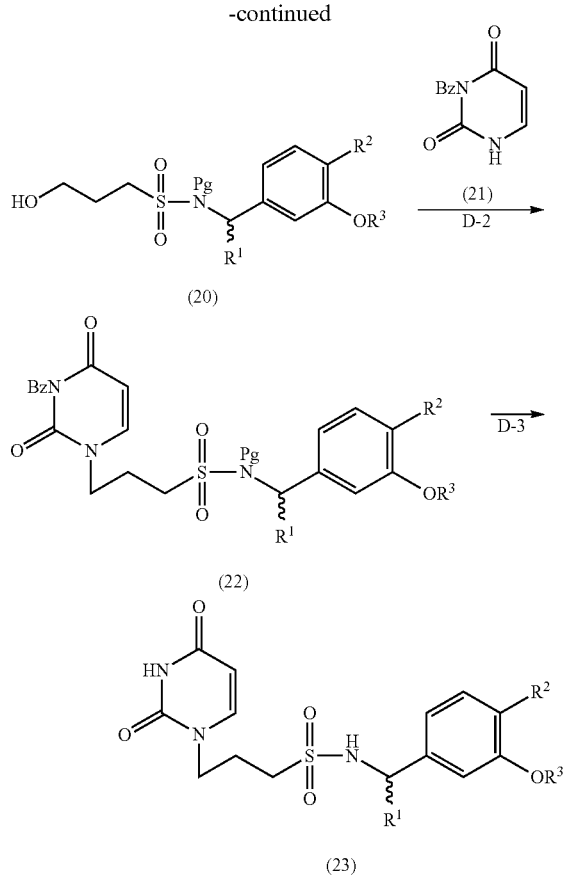

wherein $R^1$, $R^2$ and $R^3$ are as defined above; Bz represents a benzoyl group; and Pg represents a protecting group for the nitrogen atom on the sulfonamide group.

[D-1]

In this step, the nitrogen atom on the sulfonamide group of the compound represented by the general formula (17) can be protected with a protecting group, for example, a methoxymethyl group or a tert-butoxycarbonyl group, by a general method, and the resultant compound can then be reacted in the same way as in the step [C-2] to produce an alcohol compound represented by the general formula (20).

[D-2]

In this step, a 3-benzoylpyrimidine-2,4(1H, 3H)-dione (21) obtained according to the method described in the document (J. Med. Chem., 50, 6032-6038 (2007)) and the alcohol compound represented by the general formula (20) can be treated with Mitsunobu reaction in the same way as in [step A-1] (b) to produce a compound represented by the general formula (22).

[D-3]

In this step, the compound represented by the general formula (22) is debenzoylated and Pg-deprotected by a general deprotection method to produce a compound represented by the general formula (23).

The uracil compound represented by the formula (I) exhibits potent human dUTPase inhibitory activity. When the uracil compound is used in combination with various anti-tumor agents (hereinafter, referred to as anti-tumor agent A), it shows enhancing activity for anti-tumor effect of the combined anti-tumor agent A.

The type of the anti-tumor agent A whose efficacy is enhanced by the anti-tumor effect potentiator of the present invention is not particularly limited. Examples of such an anti-tumor agent A include: alkylating agents such as cyclophosphamide or nimustine; platinum-containing agents such as cisplatin, carboplatin or oxaliplatin; antimetabolites; and plant alkaloids such as paclitaxel, docetaxel or irinotecan. An antimetabolite is preferable as an anti-tumor agent A whose efficacy is enhanced by the anti-tumor effect potentiator of the present invention.

The antimetabolite used herein means a compound having a similar chemical structure to that of a natural substance used for biosynthesis of nucleic acids during cell division and proliferation of cancer cells, or a medicine containing the above defined compound as an active pharmaceutical ingredient. In other words, the antimetabolite indicates an anticancer agent which prevents the biosynthesis of nucleic acids or the biosynthetic pathway of nucleic acids and suppresses the proliferation of cancer cells. Examples thereof include: pyrimidine antimetabolites such as 5-fluorouracil (5-FU), tegafur/gimeracil/oteracil potassium (TS-1; generic name: "tegafur/gimeracil/oteracil potassium compounding agent" (brand name: "TS-1")), tegafur/uracil (UFT; generic name: "tegafur/uracil compounding agent" (brand name: "UFT")), capecitabine, doxifluridine, 5-fluoro-2'-deoxy-uridine (FdUrd), gemcitabine or cytarabine; purine antimetabolites such as fludarabine, cladribine or nelarabine; and folate antimetabolites such as pemetrexed or methotrexate. Of these, a thymidylate (TMP) synthetic pathway inhibitor is preferable. The thymidylate synthetic pathway inhibitor means a compound which directly or indirectly inhibits an enzyme associated with the biosynthesis of TMP or a medicine containing the above defined compound as an active pharmaceutical ingredient, from among antimetabolites; wherein the thymidylate synthetic pathway inhibitor includes a thymidylate synthase inhibitor and a dihydrofolate reductase inhibitor as typical examples. The thymidylate synthase inhibitor means a compound which inhibits thymidylate synthase or a medicine containing the above defined compound as an active pharmaceutical ingredient. Examples thereof include: fluoropyrimidine antimetabolites such as 5-fluorouracil (5-FU), tegafur/gimeracil/oteracil potassium (TS-1), tegafur/uracil (UFT), capecitabine, doxifluridine, 5-fluoro-2'-deoxy-uridine (FdUrd) or carmofur (Yamaful); folate antimetabolites such as pemetrexed, methotrexate or raltitrexed; and nolatrexed dihydrochloride. Moreover, the dihydrofolate reductase inhibitor means a compound which inhibits an enzyme for biosynthesizing tetrahydrofolate essential for the de novo synthesis of purines, thymidylates, etc., or a medicine containing the above defined compound as an active pharmaceutical ingredient. Examples thereof include: folate antimetabolites such as pralatrexate or edatrexate; pyrimethamine; brodimoprim; and trimetrexate glucuronate.

Anti-tumor agent A, whose action is enhanced by the anti-tumor effect potentiator of the present invention, is more preferably a thymidylate synthase inhibitor. Among such thymidylate synthase inhibitors, 5-fluorouracil (5-FU), tegafur/gimeracil/oteracil potassium (TS-1), tegafur/uracil (UFT), capecitabine, 5-fluoro-2'-deoxy-uridine (FdUrd), and pemetrexed are particularly preferable.

The type of a malignant tumor, which can be treated by a combination of the anti-tumor effect potentiator as a compound of the present invention and an anti-tumor agent A, whose anti-tumor efficacy is potentiated by the anti-tumor effect potentiator, is not particularly limited. Examples thereof include head and neck cancer, esophageal cancer, stomach cancer, colon cancer, rectal cancer, liver cancer, gallbladder cancer/biliary tract cancer, pancreatic cancer, lung cancer, breast cancer, ovarian cancer, uterine cervical cancer, endometrial cancer, renal cancer, bladder cancer, prostate cancer, testicular tumor, osteosarcoma/soft-tissue sarcoma, leukemia, malignant lymphoma, multiple myeloma, skin cancer, and encephaloma.

An anti-tumor drug having enhanced anti-tumor efficacy can be obtained by combining the uracil compound of the formula (I) or a salt thereof and the anti-tumor agent A. The form of the thus obtained novel anti-tumor drug may be either a single-agent-type preparation form containing the uracil compound of the formula (I) or a salt thereof and the anti-tumor agent A, or a separate preparation form which consists of a preparation containing the uracil compound of the formula (I) or a salt thereof and a preparation containing the anti-tumor agent A. Furthermore, route of administration for a composition containing the uracil compound of the formula (I) may be either same as, or different from, that for a composition containing the anti-tumor agent A (for example, oral administration and injection).

The anti-tumor agent A and the uracil compound of the present invention may be prepared as a kit. Individual compositions constituting the kit may be any type of known preparation forms. In general, such individual compositions may be contained various types of commonly used containers, depending on the preparation forms thereof, so as to produce a kit for treating cancers in mammals including humans.

When the uracil compound of the present invention or a pharmaceutically acceptable salt thereof is contained in a pharmaceutical composition, it may be mixed with a pharmaceutically acceptable carrier, as necessary, and may be prepared as any type of administration forms depending on preventive or therapeutic purpose. Examples of such a form include an oral agent, an injection, a suppository, an ointment, and a patch. Of these, an oral agent is preferable. These administration forms can be produced by commonly used drug formulation methods, which are known to persons skilled in the art.

Various types of organic or inorganic carrier substances, which are commonly used as materials for pharmaceutical preparations, may be used as pharmaceutically acceptable carrier. Such a pharmaceutically acceptable carrier may be mixed as a diluent, a binder, a disintegrator, a lubricant and a coloring agent in solid preparations; and a solvent, a solubilizer, a suspending agent, a tonicity agent, a buffer and a soothing agent in liquid preparations. In addition, pharmaceutical additives such as an antiseptic, an antioxidant, a coloring agent, a sweetener and a stabilizer may also be used, as necessary.

When a solid preparation for oral administration is prepared, a diluent, and as necessary, a binder, a disintegrator, a lubricant, a coloring agent, a corrigent/a flavoring agent and the like may be added to the compound of the present invention, and thereafter, the obtained mixture may be prepared as a tablet, a coated tablet, a granule, a powdery agent, a capsule and the like according to an ordinary method.

Examples of the diluent include lactose, saccharose, D-mannitol, dextrose, starch, calcium carbonate, kaoline, microcrystalline cellulose, and silicic acid anhydride.

Examples of the binder include water, ethanol, 1-propanol, 2-propanol, simple syrup, dextrose in water, pregelatinized starch solution, gelatin solution, D-mannitol, carboxymethyl cellulose, hydroxypropyl cellulose, hydroxypropyl starch, methyl cellulose, ethyl cellulose, shellac, calcium phosphate, and polyvinyl pyrrolidone.

Examples of the disintegrator include dry starch, sodium alginate, agar powders, sodium bicarbonate, calcium carbonate, sodium lauryl sulfate, monoglyceride stearate, and lactose.

Examples of the lubricant include purified talc, sodium stearate, magnesium stearate, borax, and polyethylene glycol.

Examples of the coloring agent include titanium oxide and iron oxide.

Examples of the corrigent/flavoring agent include saccharose, orange peel, citric acid, and tartaric acid.

When a liquid preparation for oral administration is prepared, a corrigent, a buffer, a stabilizer, a flavoring agent and the like may added to the compound of the present invention, and thereafter, the mixture may be prepared as an internal liquid agent, a syrup, an elixir and the like according to an ordinary method. In this case, the same corrigent/flavoring agent as those described above may be used. An example of the buffer is sodium citrate, and examples of the stabilizer include tragacanth, gum arabic, and gelatin. As necessary, these preparations for oral adiministration may be coated with enteric coating or other coating for the purpose of, for example, persistence of effects according to methods known in the field of oral preparations. Examples of such a coating agent include hydroxypropylmethyl cellulose, ethyl cellulose, hydroxymethyl cellulose, hydroxypropyl cellulose, polyoxyethylene glycol, and Tween 80 (registered trademark).

When an injection agent is prepared, a pH adjuster, a buffer, a stabilizer, a tonicity agent, a local anesthetic and the like may be added to the compound of the present invention, and the mixture may be processed into hypodermic, intramuscular and intravenous injections according to an ordinary method. Examples of the pH adjuster and the buffer used herein include sodium citrate, sodium acetate, and sodium phosphate. Examples of the stabilizer include sodium pyrosulfife, EDTA, thioglycolic acid, and thiolactic acid. Examples of the local anesthetic include procaine hydrochloride and lidocaine hydrochloride. Examples of the tonicity agent include sodium chloride, dextrose, D-mannitol, and glycerine.

When a suppository is prepared, pharmaceutically acceptable carriers known in the present field, such as polyethylene glycol, lanolin, cacao butter and fatty acid triglyceride, and as necessary, surfactants such as Tween 80 (registered trademark), may be added to the compound of the present invention, and thereafter, a suppository may be produced from the obtained mixture according to an ordinary method.

When an ointment is prepared, a commonly used base, stabilizer, wetting agent, preservative and the like may be blended into the compound of the present invention, as necessary, and the obtained mixture may be mixed to formulate an ointment according to an ordinary method. Examples of the base include liquid paraffin, white petrolatum, white beeswax, octyl dodecyl alcohol, and paraffin. Examples of the preservative include methyl paraoxybenzoate, ethyl paraoxybenzoate, and propyl paraoxybenzoate.

When a patch is prepared, the above described ointment, a cream, a gel, a paste or the like may be applied to an ordinary substrate according to an ordinary method. As a substrate, woven fabrics or non-woven fabrics consisting of cotton, spun rayon or chemical fiber; and a film or a foam sheet such as soft vinyl chloride, polyethylene or polyurethane are suitable.

The amount of the uracil compound of the present invention to be mixed into the above described each dosage unit form is not constant and varied depending on the symptoms of a patient to whom the compound is administered, the dosage form thereof, etc. In general, in the case of an oral agent, the amount of the compound is approximately 0.05 to 1000 mg per dosage unit form. In the case of an injection, the amount of the compound is approximately 0.01 to 500 mg per dosage unit form, and in the case of a suppository, the amount of the compound is approximately 1 to 1000 mg per dosage unit form.

Moreover, the daily dose amount of the medicine having the above described dosage form is not constant and may be varied depending on the symptoms, body weight, age, sex of a patient, etc. In general, its daily dose amount is approximately 0.05 to 5000 mg per adult (body weight: 50 kg) per day, and preferably 0.1 to 1000 mg per adult (body weight: 50 kg) per day. Such a dose of the medicine is preferably administered once per day, or divided into twice or three times per day.

In a case where a preparation containing the uracil compound of the formula (I) or a salt thereof is separated from a preparation containing the anti-tumor agent A, the two preparations may be administered simultaneously, or one ingredient may be administered at any time before or after the other ingredient has been administered. Preferably, the two preparations may be administered simultaneously, or one ingredient may be administered within 6 hours before or after administration of the other ingredient.

Since the uracil compound of the present invention is able to significantly potentiate the anti-tumor effect of the anti-tumor agent A, the dose amount of the anti-tumor agent A may be decreased as compared to the commonly used dose amount. Alternatively, the dose amount of the anti-tumor agent A may be the same as the commonly used dose amount.

The administration or combination ratio between the anti-tumor effect potentiator of the present invention or a salt thereof and the anti-tumor agent A is not particularly limited, as long as the ratio is within a range which can provide a potentiating effect on the anti-tumor effect. The compound of the present invention or a salt thereof may be used in an amount of approximately 0.01 to 100 moles, and preferably approximately 0.07 to 64 moles, relative to 1 mole of the anti-tumor agent A. Herein, the administration or combination ratio of the anti-tumor agent A may be determined based on the amount of an active pharmaceutical ingredient having an anti-tumor effect. For example, in the case of tegafur/gimeracil/oteracil potassium (TS-1), tegafur/uracil (UFT), etc., the compound of the present invention or a salt thereof may be used in an amount of approximately 0.01 to 100 moles, and preferably approximately 0.15 to 64 moles, relative to 1 mole of tegafur per day. In the case of capecitabine, the compound of the present invention or a salt thereof may be used in an amount of approximately 0.01 to 100 moles, and preferably approximately 0.07 to 8 moles, relative to 1 mole of capecitabine.

EXAMPLES

Hereinafter, the present invention will be described more specifically with reference to Reference Examples, Examples, and Test Examples. However, the present invention is not intended to be limited to these examples.

Reference Example 1

Synthesis of (3-(cyclopropylmethoxy)phenyl)methanamine

[Formula 6]

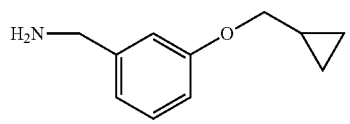

3-Cyanophenol (12.4 g) was dissolved in N,N-dimethylformamide (hereinafter, referred to as DMF; 100 mL). To the solution, potassium carbonate (30.5 g), potassium iodide (1.74 g), and (chloromethyl)cyclopropane (10.2 mL) were added, and the mixture was stirred at 90° C. for 4 hours. To the reaction mixture, water (130 mL) was added, and the resultant mixture was then extracted with toluene (130 mL). The organic layer was washed with brine (100 mL), dried over anhydrous sodium sulfate, and then concentrated under reduced pressure. The residue was dissolved in tetrahydrofuran (hereinafter, referred to as THF; 60 mL). To the solution, a solution of lithium aluminum hydride (hereinafter, referred to as LAH) in THF (2.4 M, 68 mL) was gradually added dropwise at 0° C., and the reaction mixture was then stirred at 45° C. for 4 hours. To the reaction mixture, water (10 mL), an aqueous sodium hydroxide solution (1.0 M, 10 mL), and water (5.0 mL) were gradually added at 0° C. The resultant precipitate was removed by filtration and washed with 10% methanol/THF (400 mL). Then, the combined filtrate was concentrated under reduced pressure. To the residue, water (50 mL) was added, and the resultant mixture was then extracted with ethyl acetate (50 mL×3). The organic layer was washed with brine (50 mL), dried over anhydrous sodium sulfate, and then concentrated under reduced pressure to obtain the title compound (18.1 g) as a crude product.

Reference Example 2

Synthesis of (R)-1-(3-(cyclopentyloxy)phenyl)ethanamine hydrochloride

[Formula 7]

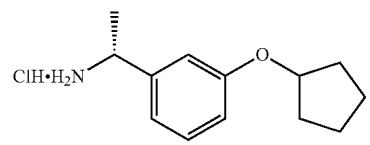

3-Hydroxybenzaldehyde (12.2 g) was dissolved in DMF (120 mL). To the solution, bromocyclopentane (32.8 mL), potassium carbonate (27.6 g), and potassium iodide (1.66 g) were added, and the mixture was stirred at 120° C. for 3.5 hours. The reaction mixture was cooled to room temperature, water (120 mL) was then added thereto, and the resultant mixture was then extracted with toluene (120 mL). The organic layer was washed with water (120 mL), an aqueous sodium hydroxide solution (1.0 M, 120 mL), and brine (100 mL), dried over anhydrous sodium sulfate, and then concentrated under reduced pressure. The residue was dissolved in toluene (250 mL). To the solution, (S)-(−)-2-methyl-2-propanesulfinamide (13.3 g) and titanium tetraisopropoxide (44.4 mL) were added, and the mixture was stirred at 70° C. for 6 hours. The reaction mixture was cooled to room temperature, and an aqueous saturated sodium bicarbonate solution (130 mL) was then added thereto. The resultant precipitate was removed by filtration and washed with ethyl acetate (200 mL×4). The combined filtrate was concentrated under reduced pressure. To the residue, brine (200 mL) was added, and the resultant mixture was then extracted with ethyl acetate (200 mL). The organic layer was dried over anhydrous magnesium sulfate and then concentrated under reduced pressure. An aliquot (1.47 g) of the residue (29.3 g) was dissolved in THF (7.5 mL). To the solution, a solution of methylmagnesium bromide in diethyl ether (3.0 M, 3.33 mL) was added dropwise at 0° C., and the mixture was stirred at 0°

C. for 4 hours. To the reaction mixture, an aqueous saturated ammonium chloride solution (6.0 mL) was added at 0° C. over 5 minutes, and the resultant mixture was then extracted with ethyl acetate (10 mL). The organic layer was washed with brine (6.0 mL), dried over anhydrous sodium sulfate, and then concentrated under reduced pressure. The residue was purified by silica gel column chromatography (40% ethyl acetate/hexane). The obtained compound (1.09 g) was dissolved in methanol (10 mL). To the solution, a hydrochloric acid-dioxane solution (4.0 M, 1.1 mL) was added, and the mixture was stirred at room temperature for 30 minutes. The reaction mixture was concentrated under reduced pressure and then the residue was co-evaporated with toluene (5.0 mL×3) to obtain the title compound (845 mg).

Reference Example 3

Synthesis of (R)-1-(3-((R)-tetrahydrofuran-3-yloxy)phenyl)ethanamine hydrochloride

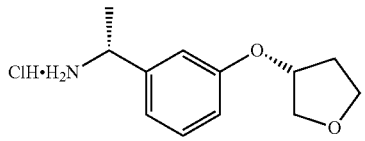

[Formula 8]

3-Hydroxybenzaldehyde (1.3 g), triphenylphosphine (3.6 g), and (S)-(+)-tetrahydro-3-furanol (1.2 mL) were dissolved in THF (20 mL). To the solution, a toluene solution of diethyl azodicarboxylate (hereinafter referred to as DEAD) (2.2 M, 6.2 mL) was gradually added dropwise at 0° C., and the mixture was then stirred at room temperature for 2 hours. The reaction mixture was concentrated under reduced pressure, and ethyl acetate (20 mL) was then added thereto. The organic layer was washed with an aqueous sodium hydroxide solution (1.0 M, 5.0 mL), dried over anhydrous sodium sulfate, and then concentrated under reduced pressure. The residue was purified by silica gel column chromatography (500 ethyl acetate/hexane). The obtained compound was dissolved in toluene (6.5 mL). To the solution, (S)-(−)-2-methyl-2-propanesulfinamide (330 mg) and titanium tetraisopropoxide (1.1 mL) were added, and the mixture was stirred at 75° C. for 6 hours. The reaction mixture was cooled to room temperature, and an aqueous saturated sodium bicarbonate solution (10 mL) was then added thereto. The resultant precipitate was removed by filtration and washed with ethyl acetate (20 mL×4). The combined filtrate was concentrated under reduced pressure. To the residue, brine (30 mL) was added, and the resultant mixture was then extracted with ethyl acetate. The organic layer was dried over anhydrous magnesium sulfate and then concentrated under reduced pressure. The residue was dissolved in THF (7.5 mL). To the solution, a solution of methylmagnesium bromide in diethyl ether (3.0 M, 1.7 mL) was added dropwise at 0° C., and the mixture was stirred at room temperature for 2 hours. To the reaction mixture, an aqueous saturated ammonium chloride solution (10 mL) was added at 0° C. over 10 minutes, and the resultant mixture was then extracted with ethyl acetate (15 mL). The organic layer was washed with brine (10 mL), dried over anhydrous sodium sulfate, and then concentrated under reduced pressure. The residue was purified by silica gel column chromatography (100% ethyl acetate). The obtained compound was dissolved in methanol (5.0 mL). To the solution, a hydrochloric acid-dioxane solution (4.0 M, 470 µL) was added, and the mixture was stirred at room temperature for 30 minutes. The reaction mixture was concentrated under reduced pressure and then the residue was co-evaporated with toluene (4.0 mL×3) to obtain the title compound (244 mg).

Reference Example 4

Synthesis of (3-(cyclopropylmethoxy)-4-fluorophenyl)methanamine

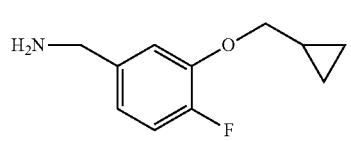

[Formula 9]

4-Fluoro-3-hydroxybenzoic acid (15.0 g) was dissolved in DMF (200 mL). To the solution, (chloromethyl)cyclopropane (18.0 mL), potassium carbonate (29.2 g), and potassium iodide (1.6 g) were added, and the mixture was stirred at 90° C. for 6 hours. The reaction mixture was cooled to room temperature, water (120 mL) was then added thereto, and the resultant mixture was then extracted with toluene (120 mL). The organic layer was washed with brine (100 mL), dried over anhydrous sodium sulfate, and then concentrated under reduced pressure. The residue was dissolved in toluene (65 mL). To the solution, a solution of diisobutylaluminum hydride in hexane (hereinafter, referred to as DIBAL) (1.0 M, 130 mL) was added dropwise at 0° C., and the reaction mixture was stirred at 0° C. for 2 hours. To the reaction mixture, water (10 mL) and an aqueous sodium hydroxide solution (1.0 M, 10 mL) were gradually added. The resultant precipitate was removed by filtration and washed with ethyl acetate (100 mL×5). Then, the combined filtrate was concentrated under reduced pressure. To the residue, water (100 mL) was added, and the resultant mixture was then extracted with ethyl acetate (150 mL). The organic layer was washed with brine (50 mL), dried over anhydrous sodium sulfate, and then concentrated under reduced pressure. The residue was purified by silica gel column chromatography (40% ethyl acetate/hexane). The obtained compound was dissolved in THF (75 mL). To the solution, diphenylphosphoryl azide (12.9 mL) and 1,8-diazabicyclo[5.4.0]-7-undecene (hereinafter, referred to as DBU) (9.4 mL) were added dropwise at room temperature, and the mixture was stirred at room temperature for 1 hour. To the reaction mixture, brine (100 mL) was added, and the aqueous layer was extracted with ethyl acetate (100 mL×2). The organic layer was washed with brine (100 mL), then dried over anhydrous sodium sulfate, and concentrated under reduced pressure. The residue was purified by silica gel column chromatography (20% ethyl acetate/hexane). The obtained compound was dissolved in THF (80 mL). To the solution, a solution of LAH in THF (2.4 M, 40 mL) was gradually added dropwise at 0° C., and the mixture was stirred at 0° C. for 1 hour. To the reaction mixture, water (5.0 mL) and aqueous sodium hydroxide solution (1.0 M, 5.0 mL) were gradually added dropwise at 0° C. The resultant precipitate was removed by filtration and washed with 10% methanol/THF (200 mL). Then, the combined filtrate was concentrated under reduced pressure. To the residue, brine (100 mL) was added, and the resultant mixture was then extracted with ethyl acetate (150 mL). The organic layer was dried over anhydrous sodium sulfate and concentrated under reduced pressure to obtain the title compound (10.5 g) as a crude product.

Reference Example 5

Synthesis of (R)-1-(3-(cyclopropylmethoxy)-4-fluorophenyl)ethanamine hydrochloride

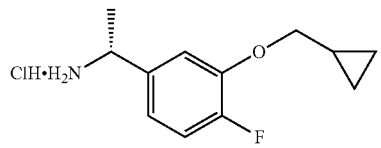

[Formula 10]

4-Fluoro-3-hydroxybenzoic acid (12.0 g) was dissolved in ethanol (200 mL). To the solution, sulfuric acid (3.5 mL) was added, and the mixture was heated to reflux at 105° C. for 4 hours. The reaction mixture was cooled to room temperature, and then concentrated under reduced pressure. To the residue, water (100 mL) and sodium carbonate (18.0 g) were added, and the aqueous layer was extracted with ethyl acetate (100 mL×2). The combined organic layer was washed with brine (100 mL), dried over anhydrous sodium sulfate, and then concentrated under reduced pressure. The residue was co-evaporated with toluene (15 mL×2), and the residue was then dissolved in DMF (100 mL). To the mixture, (chloromethyl)cyclopropane (6.9 mL), potassium carbonate (19.8 g), and potassium iodide (1.2 g) were added, and the mixture was stirred at 90° C. for 3.5 hours. The reaction mixture was cooled to room temperature, water (200 mL) was then added thereto, and the resultant mixture was then extracted with toluene (100 mL×2). The organic layer was washed with brine (100 mL), dried over anhydrous sodium sulfate, and then concentrated under reduced pressure. The residue was dissolved in THF (75 mL). To the mixture, a solution of lithium borohydride in THF (2.0 M, 54 mL) was added dropwise at room temperature, and the mixture was heated to reflux at 80° C. for 3.5 hours. The reaction mixture was cooled to 0° C., water (200 mL) was then added dropwise thereto at the same temperature, and the resultant mixture was then extracted with ethyl acetate (100 mL×2). The organic layer was washed with brine (100 mL), dried over anhydrous sodium sulfate, and then concentrated under reduced pressure. The residue was dissolved in dichloromethane (250 mL). To the mixture, manganese dioxide (86 g) was added at room temperature, and the mixture was heated to reflux at 45° C. for 6 hours. The reaction mixture was cooled to room temperature, and the precipitate was removed by filtration and washed with chloroform (100 mL×4). Then, the combined filtrate was concentrated. The residue was dissolved in toluene (150 mL). To the solution, (S)-(-)-2-methyl-2-propanesulfinamide (8.5 g) and titanium tetraisopropoxide (28.4 mL) were added, and the mixture was stirred at 75° C. for 6 hours. The reaction mixture was cooled to room temperature, and an aqueous saturated sodium bicarbonate solution (150 mL) was then added thereto. The resultant precipitate was removed by filtration and washed with ethyl acetate (200 mL×6). The combined filtrate was concentrated under reduced pressure. To the residue, brine (150 mL) was added, and the resultant mixture was then extracted with ethyl acetate (200 mL). The organic layer was dried over anhydrous magnesium sulfate and then concentrated under reduced pressure. The residue was dissolved in THF (85 mL). To the mixture, a solution of methylmagnesium bromide in diethyl ether (3.0 M, 42 mL) was added dropwise at 0° C., and the mixture was stirred at room temperature for 2 hours. To the reaction mixture, an aqueous saturated ammonium chloride solution (100 mL) was added at 0° C. over 10 minutes, and the resultant mixture was then extracted with ethyl acetate (100 mL×2). The organic layer was washed with brine (100 mL), dried over anhydrous sodium sulfate, and then concentrated under reduced pressure. The residue was purified by silica gel column chromatography (50% ethyl acetate/hexane). The obtained compound was dissolved in methanol (70 mL). To the solution, a hydrochloric acid-dioxane solution (4.0 M, 13 mL) was added, and the mixture was stirred at room temperature for 30 minutes. The reaction mixture was concentrated under reduced pressure, and the residue was then co-evaporated with toluene (40 mL×3) to obtain the title compound (9.09 g).

Reference Example 6

Synthesis of 1-(3-(cyclopropylmethoxy)phenyl)ethanamine

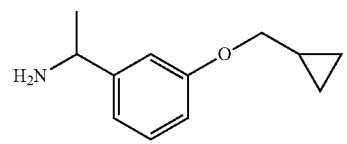

[Formula 11]

3-Hydroxybenzaldehyde (692 mg) was dissolved in DMF (25 mL). To the solution, potassium carbonate (1.56 g), potassium iodide (95 mg), and (chloromethyl)cyclopropane (578 µL) were added, and the mixture was stirred at 90° C. for 4 hours. To the reaction mixture, water (20 mL) was added, and the resultant mixture was then extracted with toluene (20 mL). The organic layer was washed with brine (20 mL), dried over anhydrous sodium sulfate, and then concentrated under reduced pressure. The residue was dissolved in THF (2.5 mL). To the mixture, a solution of methylmagnesium bromide in THF (1.0 M, 6.5 mL) was added dropwise at 0° C., and the mixture was stirred at room temperature for 2 hours. To the reaction mixture, an aqueous saturated ammonium chloride solution (10 mL) was added at 0° C., and the resultant mixture was then extracted with ethyl acetate (20 mL×2). The organic layer was washed with brine (20 mL), dried over anhydrous sodium sulfate, and then concentrated under reduced pressure. The residue was purified by silica gel column chromatography (40% ethyl acetate/hexane). The obtained compound was dissolved in THF (5.0 mL). To the solution, diphenylphosphoryl azide (875 µL) and DBU (592 µL) were added dropwise at room temperature, and the mixture was stirred for 1 hour. To the reaction mixture, brine (10 mL) was added, and the resultant mixture was then extracted with ethyl acetate (20 mL×2). The organic layer was washed with brine (10 mL), dried over anhydrous sodium sulfate, and then concentrated under reduced pressure. The residue was purified by silica gel column chromatography (20% ethyl acetate/hexane). The obtained compound was dissolved in methanol (7.5 mL). To the solution, 10% palladium-carbon (180 mg) was added, and the reaction mixture was stirred at room temperature for 2 hours under a hydrogen atmosphere. The precipitate was removed by filtration through a pad of Celite and washed with methanol (100 mL). Then, the combined filtrate was concentrated under reduced pressure to obtain the title compound (740 mg) as a crude product.

Reference Examples 7 to 19

Amines shown in the following tables were synthesized according to the method of any one of Reference Examples 1 to 3 and 5.

TABLE 1
| Reference Example | Starting Material | Amine | Production Method |
|---|---|---|---|
| 7 | 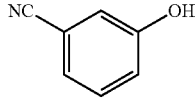 | 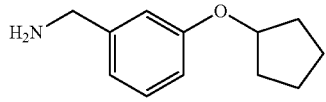 [SMILES: NCc1cccc(OC2CCCC2)c1] | 1 |
| 8 | 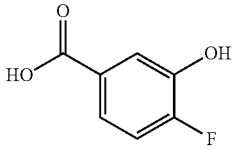 [SMILES: O=C(O)c1ccc(F)c(O)c1] | 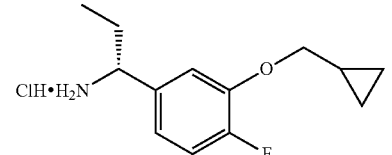 | 5 |
| 9 | 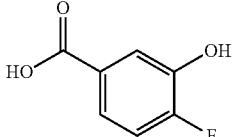 | 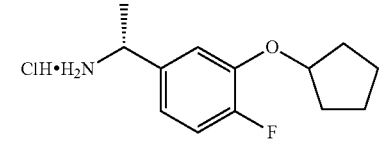 | 5 |
| 10 | 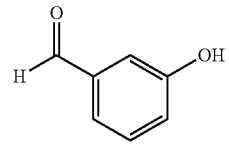 | 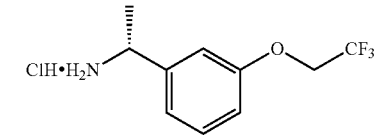 | 2 |
| 11 | 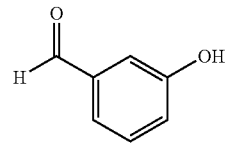 | 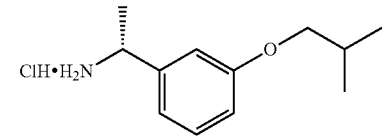 | 2 |
| 12 | 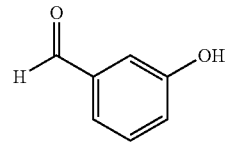 | 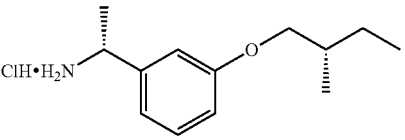 | 2 |
| 13 | 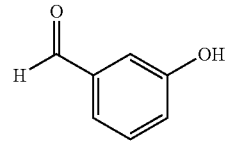 | 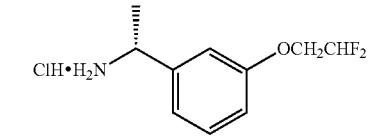 | 2 |
TABLE 2
| Reference Example | Starting Material | Amine | Production Method |
|---|---|---|---|
| 14 | 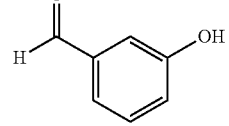 | 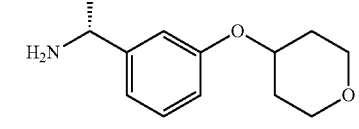 | 3 |
| 15 | 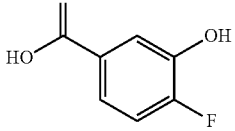 | 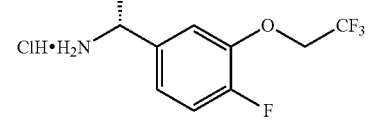 | 5 |

TABLE 2-continued

| Reference Example | Starting Material | Amine | Production Method |
|---|---|---|---|
| 16 | 3-hydroxy-4-fluoro-benzoic acid | (R)-1-(3-(2,2-difluoroethoxy)-4-fluorophenyl)ethan-1-amine·HCl | 5 |
| 17 | 3-hydroxybenzaldehyde | (R)-1-(3-(allyloxy)phenyl)ethan-1-amine·HCl | 2 |
| 18 | 3-hydroxybenzaldehyde | (R)-1-(3-(cyclopropylmethoxy)phenyl)ethan-1-amine·HCl | 2 |
| 19 | 3-hydroxybenzaldehyde | (S)-1-(3-(cyclopropylmethoxy)phenyl)propan-1-amine·HCl | 2 |

Reference Example 20

Synthesis of N-(3-(cyclopropylmethoxy)benzyl)-3-(methoxymethoxy)propane-1-sulfonamide

[Formula 12]

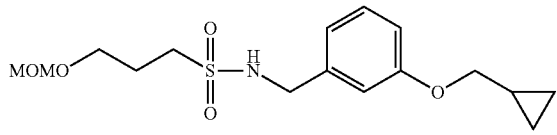

The (3-(cyclopropylmethoxy)phenyl)methanamine (10.0 g) obtained in Reference Example 1 was dissolved in dichloromethane (50 mL). To the solution, triethylamine (11.9 g) and 3-chloropropanesulfonyl chloride (10.6 g) were added at 0° C., and the mixture was stirred at room temperature for 12 hours. To the reaction mixture, water (100 mL) was added, and the resultant mixture was then extracted with chloroform (50 mL). The organic layer washed with dilute hydrochloric acid (1.0 M, 100 mL) and brine (100 ml), dried over anhydrous sodium sulfate, and then concentrated under reduced pressure. The residue was dissolved in DMF (100 mL). To the mixture, sodium acetate (10.2 g) and sodium iodide (18.6 g) were added, and the mixture was stirred at 80° C. for 8 hours. The reaction mixture was cooled to room temperature, water (100 mL) was then added thereto, and the resultant mixture was then extracted with ethyl acetate (80 mL×2). The organic layer was washed with brine (100 mL), dried over anhydrous sodium sulfate, and then concentrated under reduced pressure. The residue was purified by silica gel column chromatography (50% ethyl acetate/hexane). The obtained compound was dissolved in a 5 to 10% hydrochloric acid/methanol solution (100 mL), and the solution was heated to reflux at 80° C. for 1 hour. The reaction mixture was cooled to room temperature and then concentrated under reduced pressure. The residue was purified by silica gel column chromatography (66% ethyl acetate/hexane). The obtained compound was dissolved in dichloromethane (80 mL). To the solution, N,N-diisopropylethylamine (14.1 mL) and chloromethyl methyl ether (4.1 mL) were added, and the mixture was stirred at room temperature for 1 hour. To the reaction mixture, an aqueous saturated ammonium chloride solution (50 mL) was added, and the resultant mixture was then extracted with chloroform (50 mL). The organic layer was washed with brine (30 mL), dried over anhydrous sodium sulfate, and then concentrated under reduced pressure. The residue was purified by silica gel column chromatography (25% ethyl acetate/hexane) to obtain the title compound (11.5 g).

Reference Examples 21 to 37

The compounds shown in the following tables were synthesized according to the method of Reference Example 20.

TABLE 3

| Reference Example | Reference Example No. of Amine | Product |
| --- | --- | --- |
| 21 | 2 | MOMO-(CH2)3-SO2-NH-CH(CH3)-[3-(cyclopentyloxy)phenyl] |
| 22 | 3 | MOMO-(CH2)3-SO2-NH-CH(CH3)-[3-((S)-tetrahydrofuran-3-yloxy)phenyl] |
| 23 | 4 | MOMO-(CH2)3-SO2-NH-CH2-[4-fluoro-3-(cyclopropylmethoxy)phenyl] |
| 24 | 5 | MOMO-(CH2)3-SO2-NH-CH(CH3)-[4-fluoro-3-(cyclopropylmethoxy)phenyl] |
| 25 | 6 | MOMO-(CH2)3-SO2-NH-CH(CH3)-[3-(cyclopropylmethoxy)phenyl] |
| 26 | 7 | MOMO-(CH2)3-SO2-NH-CH2-[3-(cyclopentyloxy)phenyl] |
| 27 | 8 | MOMO-(CH2)3-SO2-NH-CH(C2H5)-[4-fluoro-3-(cyclopropylmethoxy)phenyl] |
| 28 | 9 | MOMO-(CH2)3-SO2-NH-CH(CH3)-[4-fluoro-3-(cyclopentyloxy)phenyl] |
| 29 | 10 | MOMO-(CH2)3-SO2-NH-CH(CH3)-[3-(2,2,2-trifluoroethoxy)phenyl] |

TABLE 4

| Reference Example | Reference Example No. of Amine | Product |
| --- | --- | --- |
| 30 | 11 | MOMO-(CH2)3-S(O2)-NH-CH(CH3)-[3-(OCH2CH(CH3)2)-C6H4] |
| 31 | 12 | MOMO-(CH2)3-S(O2)-NH-CH(CH3)-[3-(O-CH2-CH(CH3)-CH2CH3)-C6H4] |
| 32 | 13 | MOMO-(CH2)3-S(O2)-NH-CH(CH3)-[3-(OCH2CHF2)-C6H4] |
| 33 | 14 | MOMO-(CH2)3-S(O2)-NH-CH(CH3)-[3-(O-tetrahydropyran-4-yl)-C6H4] |
| 34 | 15 | MOMO-(CH2)3-S(O2)-NH-CH(CH3)-[4-F-3-(OCH2CF3)-C6H3] |
| 35 | 16 | MOMO-(CH2)3-S(O2)-NH-CH(CH3)-[4-F-3-(OCH2CHF2)-C6H3] |
| 36 | 17 | MOMO-(CH2)3-S(O2)-NH-CH(CH3)-[3-(OCH2CH=CH2)-C6H4] |
| 37 | 18 | MOMO-(CH2)3-S(O2)-NH-CH(CH3)-[3-(OCH2-cyclopropyl)-C6H4] |

MOM in the tables indicates a methoxymethyl group.

Reference Example 38

Synthesis of (R)—N-(1-(3-(cyclopropylmethoxy) phenyl)propyl)-3-hydroxy-N-(methoxymethyl)propane-1-sulfonamide

[Formula 13]

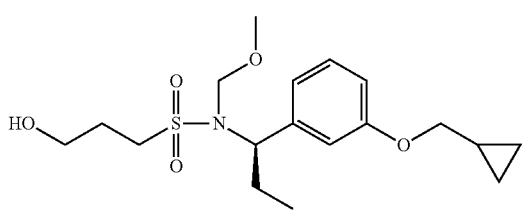

The (R)-1-(3-(cyclopropylmethoxy)phenyl)propane-1-amine hydrochloride (5.4 g) obtained in Reference Example 19 was dissolved in dichloromethane (50 mL). To the solution, triethylamine (8.7 mL) and 3-chloropropanesulfonyl chloride (2.9 mL) were added at 0° C., and the mixture was stirred at room temperature for 2 hours. To the reaction mixture, water (50 mL) was added, and the resultant mixture was then extracted with chloroform (100 mL). The organic layer was washed with brine (50 mL), dried over anhydrous sodium sulfate, and then concentrated under reduced pressure. The residue was purified by silica gel column chromatography (40% ethyl acetate/hexane). The obtained compound was dissolved in dichloromethane (50 mL). To the solution, N,N-diisopropylethylamine (22.9 mL) and chloromethyl methyl ether (6.6 mL) were added, and the mixture was stirred at 40° C. for 12 hours. To the reaction mixture, an aqueous saturated ammonium chloride solution (50 mL) was added, the resultant mixture was then extracted with chloroform (50 mL). The organic layer was washed with an aqueous saturated ammonium chloride solution (50 mL) and brine (50 mL), dried over anhydrous sodium sulfate, and then concentrated under reduced pressure. The residue was purified by silica gel column chromatography (20% ethyl acetate/hexane). The obtained compound was dissolved in DMF (50 mL). To the solution, sodium acetate (3.6 g) and sodium iodide (6.6 g) were added, and the mixture was stirred at 80° C. for 8 hours. The reaction mixture was cooled to room temperature, water (100 mL) was then added thereto, and the resultant mixture was then extracted with ethyl acetate (75 mL×2). The organic layer was washed with brine (50 mL), dried over anhydrous sodium sulfate, and then concentrated under reduced pressure. The residue was purified by silica gel column chromatography (50% ethyl acetate/hexane). The obtained compound was dissolved in a solution of methylamine in methanol (40%, 100 mL), and the mixture was stirred at room temperature for 1 hour. The reaction mixture was concentrated under reduced pressure and then purified by silica gel column chromatography (66% ethyl acetate/hexane), to obtain the titled compound (4.5 g).

Reference Example 39

Synthesis of 3-(cyclopropylmethoxy)-N-(1-(3-(methoxymethoxy)propyl)cyclopropyl)benzenesulfonamide

[Formula 14]

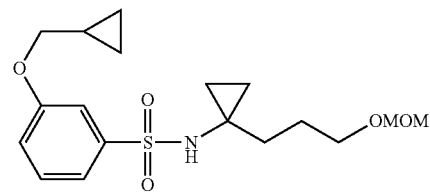

1-Aminocyclopropanepropanol hydrochloride (258 mg) obtained according to the method described in the document (J. Heterocyclic Chem., 25, 1769-1772 (1988)) was dissolved in water (850 μL) and THF (3.4 mL). To the solution, Magnesium oxide (343 mg), triethylamine (355 μL), and 3-benzoyloxybenzenesulfonyl chloride (504 mg) obtained according to the method described in the document (J. Pesticide Chem., 13, 107-115 (1988)) were added, and the mixture was stirred at room temperature for 1 hour. The precipitate was removed by filtration, and washed with ethyl acetate (50 mL). Then, the combined filtrate was concentrated under reduced pressure. To the residue, water (15 mL) was added, and the resultant mixture was then extracted with ethyl acetate (20 mL). The organic layer was washed with brine (10 mL), dried over anhydrous sodium sulfate, and then concentrated under reduced pressure. The residue was purified by silica gel column chromatography (75% ethyl acetate/hexane). An aliquot (520 mg) of the obtained compound (530 mg) was dissolved in dichloromethane (5.0 mL). To the solution, N,N-diisopropylethylamine (847 μL) and chloromethyl methyl ether (264 μL) were added, and the mixture was stirred at room temperature for 1.5 hours. To the reaction mixture, an aqueous saturated ammonium chloride solution (20 mL) was added, and the resultant mixture was extracted with ethyl acetate (20 mL). The organic layer was washed with an aqueous saturated ammonium chloride solution (20 mL) and brine (20 mL), dried over anhydrous sodium sulfate, and then concentrated under reduced pressure. The residue was purified by silica gel column chromatography (20% ethyl acetate/hexane). An aliquot (440 mg) of the obtained compound (446 mg) was dissolved in a solution of methylamine in methanol (40%, 5.0 mL), and the mixture was stirred at room temperature for 20 minutes. The reaction mixture was concentrated under reduced pressure, and the residue was then dissolved in DMF (9.0 mL). To the solution, Potassium carbonate (290 mg), potassium iodide (17 mg), and (chloromethyl)cyclopropane (107 μL) were added, and the mixture was stirred at 90° C. for 16 hours. The reaction mixture was cooled to room temperature, and water (30 mL) was added thereto, and the resultant mixture with ethyl acetate (30 mL). The organic layer was washed with water (20 mL) and brine (20 mL), dried over anhydrous sodium sulfate, and then concentrated under reduced pressure. The residue was purified by silica gel column chromatography (20% ethyl acetate/hexane) to obtain the titled compound (312 mg) as a pale yellow oil.

Example 1

Synthesis of N-(3-(cyclopropylmethoxy)benzyl)-3-((2,4-dioxo-3,4-dihydropyrimidin-1(2H)-yl)methoxy)propane-1-sulfonamide

[Formula 15]

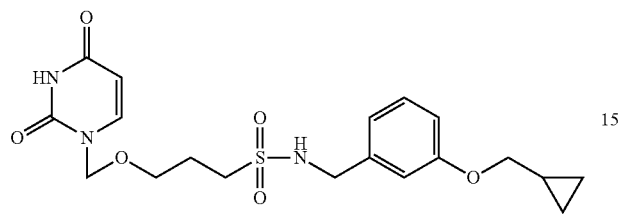

The N-(3-(cyclopropylmethoxy)benzyl)-3-(methoxymethoxy)propane-1-sulfonamide (6.8 g) obtained in Reference Example 20 was dissolved in dichloromethane (20 mL). To the solution, a solution of boron trichloride (hereinafter referred to as $BCl_3$) in dichloromethane (1.0 M, 6.7 mL) was added at 0° C., and the mixture was stirred at room temperature for 1.5 hours. The reaction mixture was concentrated under reduced pressure, and the residue was dissolved in 1,2-dichloroethane (hereinafter referred to as DCE, 25 mL).

2,4-Bis(trimethylsilyloxy)pyrimidine (7.1 g) obtained according to a method described in the document (Nucleosides & Nucleotides, 4, 565-585 (1985)) was dissolved in DCE (150 mL). To the solution, the DCE solution (25 mL) of the above residue and iodine (180 mg) were added, and the mixture was heated to reflux at 95° C. for 3.5 hours. The reaction mixture was cooled to room temperature, water (350 mL) and an aqueous saturated sodium thiosulfate solution (10 mL) were then added thereto, and the resultant mixture was then extracted with 10% methanol/chloroform (100 mL×3). The combined organic layer was washed with brine (150 mL), dried over anhydrous sodium sulfate, and then concentrated under reduced pressure. The residue was purified by silica gel column chromatography (100% ethyl acetate) to obtain the title compound (3.5 g, yield: 42%) as a white solid.

$^1$H-NMR (CDCl$_3$) δ (ppm): 0.30-0.39 (2H, m), 0.57-0.68 (2H, m), 1.20-1.31 (1H, m), 1.96-2.09 (2H, m), 3.0 (2H, t, J=7.2 Hz), 3.57-3.64 (2H, m), 3.81 (2H, d, J=6.9 Hz), 4.25 (2H, d, J=6.1 Hz), 4.89 (1H, brs), 5.09 (2H, s), 5.75 (1H, dd, J=7.9, 1.8 Hz), 6.76-6.90 (3H, m), 7.20-7.29 (2H, m), 8.90 (1H, brs)

Example 2 to Example 18

The following compounds were synthesized according to the method of Example 1 from the compounds obtained in Reference Examples 21 to 37, respectively. The results are shown in the following tables.

Example 2

(R)—N-(1-(3-(cyclopentyloxy)phenyl)ethyl)-3-((2,4-dioxo-3,4-dihydropyrimidin-1(2H)-yl)methoxy)propane-1-sulfonamide

Example 3

3-((2,4-dioxo-3,4-dihydropyrimidin-1(2H)-yl)methoxy)-N—((R)-1-(3-((R)-tetrahydrofuran-3-yloxy)phenyl)ethyl)propane-1-sulfonamide

Example 4

N-(3-(cyclopropylmethoxy)-4-fluorobenzyl)-3-((2,4-dioxo-3,4-dihydropyrimidin-1(2H)-yl)methoxy)propane-1-sulfonamide

Example 5

(R)—N-(1-(3-(cyclopropylmethoxy)-4-fluorophenyl)ethyl)-3-((2,4-dioxo-3,4-dihydropyrimidin-1(2H)-yl)methoxy)propane-1-sulfonamide

Example 6

N-(1-(3-(cyclopropylmethoxy)phenyl)ethyl)-3-((2,4-dioxo-3,4-dihydropyrimidin-1(2H)-yl)methoxy)propane-1-sulfonamide

Example 7

N-(3-(cyclopentyloxy)benzyl)-3-((2,4-dioxo-3,4-dihydropyrimidin-1(2H)-yl)methoxy)propane-1-sulfonamide

Example 8

(R)—N-(1-(3-(cyclopropylmethoxy)-4-fluorophenyl)propyl)-3-((2,4-dioxo-3,4-dihydropyrimidin-1(2H)-yl)methoxy)propane-1-sulfonamide

Example 9

(R)—N-(1-(3-(cyclopentyloxy)-4-fluorophenyl)ethyl)-3-((2,4-dioxo-3,4-dihydropyrimidin-1(2H)-yl)methoxy)propane-1-sulfonamide

Example 10

(R)-3-((2,4-dioxo-3,4-dihydropyrimidin-1(2H)-yl)methoxy)-N-(1-(3-(2,2,2-trifluoroethoxy)phenyl)ethyl)propane-1-sulfonamide

Example 11

(R)-3-((2,4-dioxo-3,4-dihydropyrimidin-1(2H)-yl)methoxy)-N-(1-(3-isobutoxyphenyl)ethyl)propane-1-sulfonamide

Example 12

3-((2,4-dioxo-3,4-dihydropyrimidin-1(2H)-yl)methoxy)-N—((R)-1-(3-((S)-2-methylbutoxy)phenyl)ethyl)propane-1-sulfonamide

Example 13

(R)—N-(1-(3-(2,2-difluoroethoxy)phenyl)ethyl)-3-((2,4-dioxo-3,4-dihydropyrimidin-1(2H)-yl)methoxy)propane-1-sulfonamide

Example 14

(R)-3-((2,4-dioxo-3,4-dihydropyrimidin-1(2H)-yl)methoxy)-N-(1-(3-(tetrahydro-2H-pyran-4-yloxy)phenyl)ethyl)propane-1-sulfonamide

Example 15

(R)-3-((2,4-dioxo-3,4-dihydropyrimidin-1(2H)-yl)methoxy)-N-(1-(4-fluoro-3-(2,2,2-trifluoroethoxy)phenyl)ethyl)propane-1-sulfonamide

Example 16

(R)—N-(1-(3-(2,2-difluoroethoxy)-4-fluorophenyl)ethyl)-3-((2,4-dioxo-3,4-dihydropyrimidin-1(2H)-yl)methoxy)propane-1-sulfonamide

Example 17

(R)—N-(1-(3-(allyloxy)phenyl)ethyl)-3-((2,4-dioxo-3,4-dihydropyrimidin-1(2H)-yl)methoxy)propane-1-sulfonamide

Example 18

(R)—N-(1-(3-(cyclopropylmethoxy)phenyl)ethyl)-3-((2,4-dioxo-3,4-dihydropyrimidin-1(2H)-yl)methoxy)propane-1-sulfonamide

TABLE 5

| Example | Reference Example No. | Product | Yield (%) | $^1$H-NMR δ (ppm) |
|---|---|---|---|---|
| 2 | 21 | | 44 | (CDCl$_3$) 1.53 (3H, d, J = 6.8 Hz), 1.56-1.98 (10H, m), 2.67-2.78 (1H, m), 2.80-2.91 (1H, m), 3.42-3.60 (2H, m), 4.51-4.63 (2H, m), 4.74-4.89 (1H, m), 5.05 (2H, s), 5.76 (1H, dd, J = 7.8, 2.2 Hz), 6.77-6.89 (3H, m), 7.20-7.27 (2H, m), 8.31 (1H, brs) Foam |
| 3 | 22 | | 41 | (CDCl$_3$) 1.52 (3H, d, J = 6.8 Hz), 1.85-1.92 (2H, m), 2.10-2.29 (2H, m), 2.68-2.88 (2H, m), 3.43-3.56 (2H, m), 3.89-4.04 (4H, m), 4.53-4.61 (1H, m), 4.92-4.96 (1H, m), 5.05 (2H, s), 5.12 (1H, d, J = 7.0 Hz), 5.76 (1H, d, J = 8.1 Hz), 6.75-6.92 (3H, m), 7.20-7.29 (2H, m), 9.11 (1H, brs) Foam |
| 4 | 23 | | 27 | (CDCl$_3$) 0.31-0.40 (2H, m), 0.55-0.69 (2H, m), 1.19-1.36 (1H, m), 1.90-2.10 (2H, m), 2.98 (2H, t, J = 7.8 Hz), 3.62 (2H, t, J = 5.9 Hz), 3.87 (2H, d, J = 6.8 Hz), 4.21 (2H, d, J = 5.9 Hz), 5.09 (2H, s), 5.28-5.39 (1H, m), 5.77 (1H, d, J = 7.8 Hz), 6.77-7.09 (3H, m), 7.29 (1H, d, J = 8.1 Hz), 9.51 (1H, brs) Foam |
| 5 | 24 | | 46 | (CDCl$_3$) 0.31-0.38 (2H, m), 0.59-0.69 (2H, m), 1.20-1.38 (1H, m), 1.52 (3H, d, J = 6.8 Hz), 1.80-1.98 (2H, m), 2.51-2.88 (2H, m), 3.53 (2H, t, J = 5.9 Hz), 3.88 (2H, d, J = 7.0 Hz), 4.51-4.62 (1H, m), 5.06 (2H, s), 5.14 (1H, d, J = 6.8 Hz), 5.77 (1H, dd, J = 8.1 Hz, 1.6 Hz), 6.85-7.11 (3H, m), 7.29 (1H, d, J = 7.0 Hz), 9.12 (1H, brs) Foam |

TABLE 6

| Example | Reference Example No. | Product | Yield (%) | ¹H-NMR δ (ppm) |
|---|---|---|---|---|
| 6 | 25 | 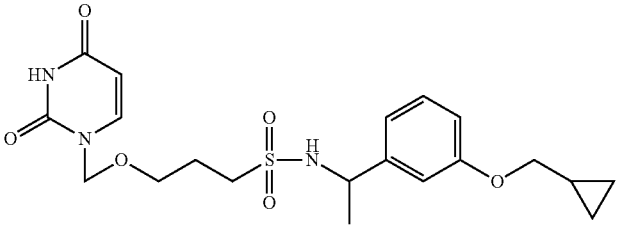 [SMILES: CC(NS(=O)(=O)CCCOCn1ccc(=O)[nH]c1=O)c1cccc(OCC2CC2)c1] | 52 | (CDCl₃) 0.31-0.38 (2H, m), 0.59-0.67 (2H, m), 1.19-1.30 (1H, m), 1.52 (2H, d, J = 6.8 Hz), 1.78-2.00 (2H, m), 2.63-2.94 (2H, m), 3.44-3.59 (2H, m), 3.81 (2H, d, J = 6.8 Hz), 4.51-4.62 (1H, m), 4.84-4.91 (1H, m), 5.06 (2H, s), 5.14 (1H, d, J = 6.8 Hz), 5.77 (1H, dd, J = 8.1, 2.2 Hz), 6.85-7.05 (3H, m), 7.20-7.30 (2H, m), 8.69 (1H, brs) Foam |
| 7 | 26 | 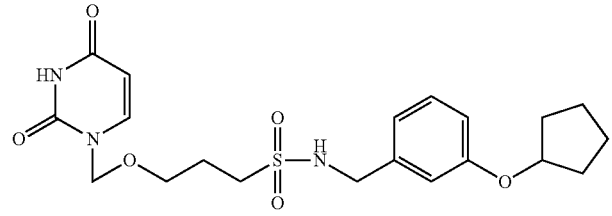 [SMILES: O=c1ccn(COCCCS(=O)(=O)NCc2cccc(OC3CCCC3)c2)c(=O)[nH]1] | 38 | (CDCl₃) 1.68-1.97 (8H, m), 1.98-2.16 (2H, m), 2.92-3.08 (2H, m), 3.60-3.69 (2H, m), 4.25 (2H, d, J = 6.1 Hz), 4.74-4.79 (2H, m), 5.01 (2H, s), 5.76 (1H, dd, J = 7.9, 2.1 Hz), 6.78-6.90 (3H, m), 7.19-7.29 (2H, m), 8.66 (1H, brs) Foam |
| 8 | 27 | 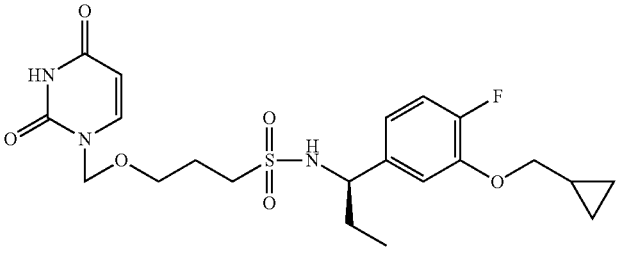 [SMILES: CC[C@@H](NS(=O)(=O)CCCOCn1ccc(=O)[nH]c1=O)c1ccc(F)c(OCC2CC2)c1] | 44 | (CDCl₃) 0.32-0.39 (2H, m), 0.63-0.71 (2H, m), 0.89 (3H, t, J = 7.3 Hz), 1.20-1.38 (1H, m), 1.71-1.99 (4H, m), 2.53-2.89 (2H, m), 3.41-3.50 (2H, m), 3.88 (2H, d, J = 7.1 Hz), 4.21-4.38 (1H, m), 5.04 (2H, s), 5.12 (1H, d, J = 7.1 Hz), 5.78 (1H, dd, J = 7.9, 2.0 Hz), 6.75-7.09 (3H, m), 7.20 (1H, d, J = 7.9 Hz), 8.97 (1H, brs) Foam |
| 9 | 28 | 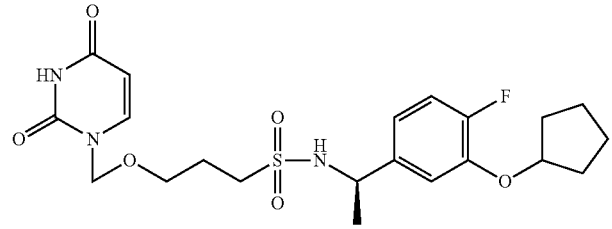 [SMILES: C[C@@H](NS(=O)(=O)CCCOCn1ccc(=O)[nH]c1=O)c1ccc(F)c(OC2CCCC2)c1] | 40 | (CDCl₃) 1.52 (3H, d, J = 7.0 Hz), 1.61-1.70 (2H, m), 1.76-2.00 (8H, m), 2.65-2.90 (2H, m), 3.53 (2H, t, J = 5.9 Hz), 4.52-4.61 (1H, m), 4.77-4.85 (1H, m), 5.05 (2H, s), 5.06-5.11 (1H, m), 5.77 (1H, dd, J = 8.1, 2.2 Hz), 6.92-7.04 (3H, m), 7.19 (1H, d, J = 8.1 Hz), 9.04 (1H, brs) Foam |

TABLE 7

| Example | Reference Example No. | Product | Yield (%) | ¹H-NMR δ (ppm) |
|---|---|---|---|---|
| 10 | 29 | 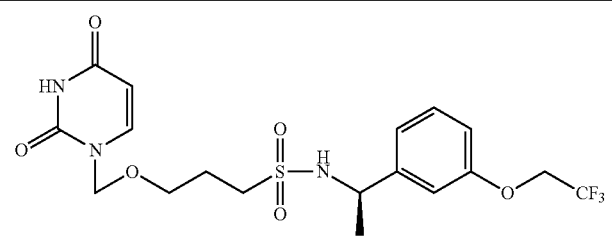 | 46 | (DMSO-d₆) 1.37 (3H, d, J = 6.8 Hz), 1.69-1.80 (2H, m), 2.58-2.70 (1H, m), 2.72-2.88 (1H, m), 3.31-3.46 (2H, m), 4.39-4.45 (1H, m), 4.69-4.79 (2H, m), 4.99 (2H, s), 5.60 (1H, dd, J = 8.1, 0.8 Hz), 6.91-7.08 (3H, m), 7.26-7.31 (1H, m), 7.63 (1H, dd, J = 8.1, 0.8 Hz), 7.73 (1H, d, J = 8.6 Hz), 11.3 (1H, brs) Foam |

TABLE 7-continued

| Example | Reference Example No. | Product | Yield (%) | $^1$H-NMR δ (ppm) |
|---|---|---|---|---|
| 11 | 30 | | 54 | (CDCl$_3$) 1.01 (6H, d, J = 6.8 Hz), 1.52 (3H, d, J = 7.0 Hz), 1.82-1.96 (2H, m), 2.00-2.09 (1H, m), 2.65-2.90 (2H, m), 3.48-3.59 (2H, m), 3.71 (2H, d, J = 6.5 Hz), 4.50-4.57 (1H, m), 5.04 (2H, s), 5.50 (1H, d, J = 7.0 Hz), 5.75 (1H, d, J = 7.8 Hz), 6.79-6.90 (3H, m), 7.17-7.29 (2H, m), 8.90 (1H, brs) Foam |
| 12 | 31 | | 48 | (CDCl$_3$) 0.95 (3H, t, J = 7.4 Hz), 1.02 (3H, d, J = 6.8 Hz), 1.53 (3H, d, J = 6.8 Hz), 1.54-1.62 (2H, m), 1.80-1.93 (3H, m), 2.67-2.88 (2H, m), 3.47-3.56 (2H, m), 3.71-3.88 (2H, m), 4.53-4.62 (1H, m), 5.05 (2H, s), 5.06 (1H, brs), 5.78 (1H, d, J = 7.9 Hz), 6.79-6.92 (3H, m), 7.22-7.31 (2H, m), 9.09 (1H, brs) Foam |
| 13 | 32 | | 40 | (DMSO-d$_6$) 1.37 (3H, d, J = 6.8 Hz), 1.61-1.84 (2H, m), 2.53-2.67 (1H, m), 2.71-2.90 (1H, m), 3.31-3.40 (2H, m), 4.23-4.46 (3H, m), 4.99 (2H, s), 5.60 (1H, d, J = 7.8 Hz), 6.39 (1H, tt, J = 54.6, 3.5 Hz), 6.86-7.03 (3H, m), 7.23-7.30 (1H, m), 7.62 (1H, d, J = 7.8 Hz), 7.73 (1H, d, J = 8.6 Hz), 11.3 (1H, brs) Foam |

TABLE 8

| Example | Reference Example No. | Product | Yield (%) | $^1$H-NMR δ (ppm) |
|---|---|---|---|---|
| 14 | 33 | | 20 | (CDCl$_3$) 1.53 (3H, d, J = 7.0 Hz), 1.71-2.10 (6H, m), 2.64-2.91 (2H, m), 3.51-3.66 (4H, m), 3.92-4.05 (2H, m), 4.48-4.59 (2H, m), 5.06 (2H, s), 5.16 (1H, d, J = 6.8 Hz), 5.76 (1H, d, J = 8.1 Hz), 6.81-6.92 (3H, m), 7.21-7.27 (2H, m), 9.22 (1H, brs) Foam |
| 15 | 34 | | 48 | (DMSO-d$_6$) 1.37 (3H, d, J = 6.8 Hz), 1.69-1.80 (2H, m), 2.56-2.90 (2H, m), 3.38-3.43 (2H, m), 4.37-4.48 (1H, m), 4.74-4.89 (2H, m), 5.00 (2H, s), 5.60 (1H, d, J = 7.8 Hz), 7.03-7.09 (1H, m), 7.20-7.32 (2H, m), 7.63 (1H, d, J = 7.8 Hz), 7.71 (1H, d, J = 8.4 Hz), 11.3 (1H, brs) Foam |

TABLE 8-continued

| Example | Reference Example No. | Product | Yield (%) | $^1$H-NMR δ (ppm) |
|---|---|---|---|---|
| 16 | 35 | (structure) | 45 | (DMSO-$d_6$) 1.37 (3H, d, J = 6.8 Hz), 1.61-1.84 (2H, m), 2.67-2.90 (2H, m), 3.42 (2H, t, J = 6.2 Hz), 4.31-4.48 (3H, m), 5.00 (2H, s), 5.60 (1H, d, J = 7.8 Hz), 6.42 (1H, tt, J = 54, 3.5 Hz), 6.98-7.04 (1H, m), 7.16-7.31 (2H, m), 7.64 (1H, d, J = 7.8 Hz), 7.71 (1H, d, J = 8.6 Hz), 11.3 (1H, brs) Foam |
| 17 | 36 | (structure) | 35 | (DMSO-$d_6$) 1.35 (3H, d, J = 7.0 Hz), 1.67-1.77 (2H, m), 2.49-2.60 (1H, m), 2.75-2.95 (1H, m), 3.25-3.40 (2H, m), 4.36-4.45 (1H, m), 4.52-4.55 (2H, m), 4.97 (2H, s), 5.24 (1H, d, J = 10.5 Hz), 5.38 (1H, d, J = 16.7 Hz), 5.59 (1H, d, J = 7.8 Hz), 5.95-6.08 (1H, m), 6.78-6.96 (3H, m), 7.17-7.24 (1H, m), 7.61 (1H, d, J = 7.8 Hz), 7.72 (1H, d, J = 8.6 Hz), 11.3 (1H, brs) Foam |

TABLE 9

| Example | Reference Example No. | Product | Yield (%) | $^1$H-NMR δ (ppm) |
|---|---|---|---|---|
| 18 | 37 | (structure) | 40 | (CDCl$_3$) 0.31-0.38 (2H, m), 0.59-0.67 (2H, m), 1.19-1.30 (1H, m), 1.52 (3H, d, J = 6.8 Hz), 1.78-2.00 (2H, m), 2.51-2.88 (2H, m), 3.44-3.59 (2H, m), 3.88 (2H, d, J = 7.0 Hz), 4.51-4.62 (1H, m), 5.06 (2H, s), 5.14 (1H, d, J = 7.0 Hz), 5.77 (1H, d, J = 7.8 Hz), 6.85-6.99 (3H, m), 7.20-7.30 (2H, m), 9.12 (1H, brs) Foam |

Example 19

Synthesis of (R)—N-(1-(3-(cyclopropylmethoxy)phenyl)propyl)-3-(2,4-dioxo-3,4-dihydropyrimidin-1(2H)-yl)propane-1-sulfonamide

[Formula 16]

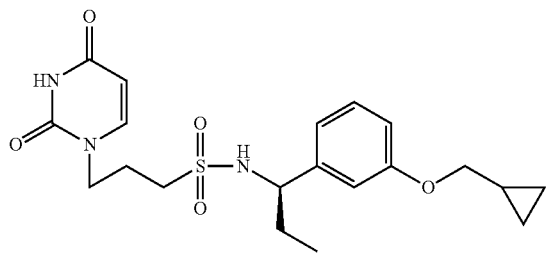

The (R)—N-(1-(3-(cyclopropylmethoxy)phenyl)propyl)-3-hydroxy-N-(methoxymethyl)propane-1-sulfonamide (4.5 g) obtained in Reference Example 38 was dissolved in THF (70 mL). To the solution, triphenylphosphine (4.48 g) and 3-benzoylpyrimidine-2,4(1H, 3H)-dione (3.6 g) obtained according to a method described in the document (J. Med. Chem., 50, 6032-6038 (2007)) were added, and the mixture was stirred at room temperature for 5 minutes. To the reaction mixture, a solution of DEAD in toluene (2.2 M, 7.6 mL) was gradually added dropwise, and the mixture was stirred at room temperature for 4 hours. The reaction mixture was concentrated under reduced pressure, and the residue was then purified by silica gel column chromatography (70% ethyl acetate/hexane). The obtained compound was dissolved in a solution of methylamine in methanol (40%, 80 mL), and the mixture was stirred at room temperature for 30 minutes. The reaction mixture was concentrated under reduced pressure, and the residue was then purified by silica gel column chromatography (100% ethyl acetate). The obtained compound was dissolved in dioxane (25 mL). To the solution, a hydrochloric acid-dioxane solution (4.0 M, 25 mL) was added, and the mixture was stirred at room temperature for 1 hour. The reaction mixture was neutralized by the addition of an aqueous saturated sodium bicarbonate solution (40 mL) at 0° C., and was then extracted with ethyl acetate (50 mL×2). The organic layer was washed with brine (50 mL), dried over anhydrous sodium sulfate, and then concentrated under reduced pressure. The residue was purified by silica gel column chromatography (100% ethyl acetate) to obtain the title compound (2.0 g, yield: 39%).

$^1$H-NMR (CDCl$_3$) δ (ppm): 0.35-0.38 (2H, m), 0.62-0.70 (2H, m), 0.90 (3H, t, J=7.3 Hz), 1.22-1.32 (1H, m), 1.75-2.01 (4H, m), 2.53-2.64 (2H, m), 3.57-3.79 (2H, m), 3.80 (2H, d, J=6.8 Hz), 4.26-4.32 (1H, m), 4.80 (1H, brs), 5.65 (1H, d, J=7.8 Hz), 6.82 (2H, d, J=7.0 Hz), 7.10 (1H, d, J=7.8 Hz), 7.22-7.29 (2H, m), 9.11 (1H, brs)

Comparative Compound 1

Synthesis of 3-(cyclopropylmethoxy)-N-(1-(3-((2,4-dioxo-3,4-dihydropyrimidin-1(2H)-yl)methoxy)propyl)cyclopropyl)benzenesulfonamide

[Formula 17]

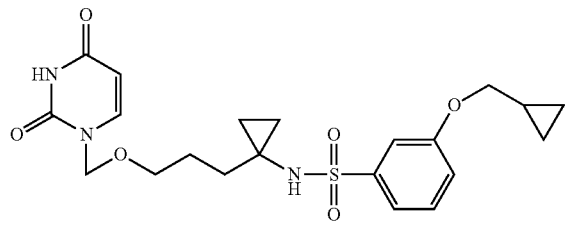

The 3-(cyclopropylmethoxy)-N-(1-(3-(methoxymethoxy)propyl)cyclopropyl)benzenesulfonamide (308 mg) obtained in Reference Example 39 was dissolved in dichloromethane (1.0 mL). To the solution, a solution of BCl$_3$ in dichloromethane (1.0 M, 300 μL) was gradually added at 0° C., and the mixture was stirred at room temperature for 2 hours. The reaction mixture was concentrated under reduced pressure, and the residue was then dissolved in DCE (8.0 mL). To the mixture, 2,4-bis(trimethylsilyloxy)pyrimidine (319 mg) obtained according to a method described in the document (Nucleosides & Nucleotides, 4, 565-585 (1985)) and iodine (8.0 mg) were added, and the mixture was heated to reflux at 93° C. for 1.5 hours. The reaction mixture was cooled to room temperature, an aqueous saturated sodium bisulfite solution (5.0 mL) was then added thereto, and the resultant mixture was then extracted with ethyl acetate (20 mL). The organic layer was washed with brine (10 mL), dried over anhydrous sodium sulfate, and then concentrated under reduced pressure. The residue was purified by silica gel column chromatography (90% ethyl acetate/hexane) to obtain the title compound (210 mg, yield: 56%) as a pale yellow gum.

$^1$H-NMR (DMSO-d$_6$) δ (ppm): 0.30-0.37 (4H, m), 0.50-0.60 (4H, m), 1.18-24 (3H, m), 1.46-1.52 (2H, m), 3.21-3.27 (2H, m), 3.85 (2H, d, J=6.9 Hz), 4.97 (2H, s), 5.59 (1H, d, J=7.9 Hz), 7.12-7.16 (1H, m), 7.24-7.32 (2H, m), 7.40-7.46 (1H, m), 7.61 (1H, d, J=7.9 Hz), 8.04 (1H, brs), 11.30 (1H, brs)

Test Example 1

Human dUTPase Inhibitory Effect

The inhibitory activity of these compounds of the present invention against human dUTPase was determined by measuring the production of [5-$^3$H]deoxyuridine monophosphate (hereinafter, referred to as [5-$^3$H]dUMP) from [5-$^3$H]deoxyuridine triphosphate (hereinafter, referred to as [5-$^3$H]dUTP) according to a method shown below.

Specifically, 0.2 mL in total of a solution containing 0.02 mL of 1 μM dUTP (including 588 Bq/mL [5-$^3$H]dUTP), 0.05 mL of a 0.2 M Tris buffer solution (pH 7.4), 0.05 mL of 16 mM magnesium chloride, 0.02 mL of 20 mM 2-mercaptoethanol, 0.02 mL of a 1% aqueous solution of fetal bovine serum-derived albumin, 0.02 mL of varying concentrations of test compound solutions or pure water as a control, and 0.02 mL of a solution of human dUTPase, which is expressed in *E. coli* and then purified, was incubated at 37° C. for 15 minutes. After the incubation, the solution was heated at 100° C. for 1 minute to terminate the reaction, followed by centrifugation at 15000 rpm for 2 minutes. An aliquot (150 μL) of the supernatant obtained by centrifugation was analyzed using an Atlantis dC18 column (manufactured by Waters Corp., 4.6× 250 mm) and a high-performance liquid chromatograph (manufactured by Shimadzu Corp., Prominence). Samples were analyzed at a flow rate of 0.8 mL/min for 30 minutes by a gradient from a 4:6 mixed solution A (10 mM potassium dihydrogen phosphate (pH 6.7), 10 mM tetrabutylammonium, and 0.25% methanol) and a solution B (50 mM potassium dihydrogen phosphate (pH 6.7), 5.6 mM tetrabutylammonium, and 30% methanol) to the 100% of solution B. The eluate was mixed with a scintillator (manufactured by PerkinElmer Co., Ltd., Ultima-Flo AP) at a 1:2 ratio, and the radioactivity of [5-$^3$H]dUMP(RT 10.2 min) was detected by Radiomatic Flow Scintillation Analyzer (manufactured by PerkinElmer Co., Ltd., 525TR).

The inhibitory activity of the test compound was determined according to the formula shown below. A concentration at which the test solution inhibits 50% of [5-$^3$H]dUMP production by human dUTPase is shown as IC$_{50}$ (μM) in Tables 10.

Inhibitory rate (%) = [Number 1]

$$\left(1 - \frac{\text{Amount of } [5-^3H] \, dUMP \text{ in the presence of test solution } (dpm)}{\text{Amount of } [5-^3H]dUMP \text{ as control } (dpm)}\right) \times 100$$

The human dUTPase inhibitory activity is shown in the following table.

TABLE 10

| Compound No. | IC$_{50}$ (μM) |
|---|---|
| Compound 1 | 0.33 |
| Compound 2 | 0.06 |
| Compound 3 | 0.46 |
| Compound 4 | 0.64 |
| Compound 5 | 0.09 |
| Compound 6 | 0.49 |
| Compound 7 | 0.27 |
| Compound 8 | 0.03 |
| Compound 9 | 0.04 |
| Compound 10 | 0.23 |
| Compound 11 | 0.31 |
| Compound 12 | 0.72 |
| Compound 13 | 0.14 |
| Compound 14 | 0.21 |
| Compound 15 | 0.23 |
| Compound 16 | 0.11 |
| Compound 17 | 0.74 |
| Compound 18 | 0.05 |
| Compound 19 | 0.61 |
| Comparative Compound 1 | 0.13 |

Test Example 2

Enhancing Activity of Compounds of the Present Invention for Anti-Tumor Effect of TS-1

A human breast cancer cell line MX-1 was transplanted into the right-sided chest of 5- to 6-week-old male BALB/cA Jcl-nu mice. After transplantation, the major axis (mm) and minor axis (mm) of the tumor were measured, and the tumor volume (TV) was estimated by calculation. Using MiSTAT group separation program, the mice were then divided into individual groups so that the mean TV of each group is to be equal. The date at which mice were divided into the groups (n=5) was defined as day 0.

A test solution for tegafur/gimeracil/oteracil potassium (TS-1, manufactured by Taiho Pharmaceutical Co., Ltd.) single administration group, containing 0.5% hydroxypropylmethyl cellulose, 2.5% dimethylacetamide, 2.5% Tween 80, and 10% Cremophor as final concentrations, was prepared, provided at 8.3 mg/kg/day. The dose of TS-1 was represented by the amount of tegafur (FT).

A test solution for combined administration group (TS-1+ the compound of the present invention) was prepared in the same manner as the aforementioned test solution for the TS-1 single administration group, specifically, 200 mg/kg/day test drug+TS-1 (8.3 mg/kg/day) in the case of the Compounds 6, 4, 7 and 8 of the present invention, 100 mg/kg/day test drug+TS-1 (8.3 mg/kg/day) in the case of the Compounds 19, 9, 2 and 1 of the present invention, and 200 mg/kg/day test drug+TS-1 (8.3 mg/kg/day) in the case of the Comparative Compound 1.

Each test solution was orally administered to mouse at 10 mL/kg volume of solution every day for 14 days from day 1.

TV on day 15 was measured, and relative tumor volume (RTV) was calculated. Then, T/C (%) was calculated according to a formula described below, and an anti-tumor effect was evaluated. The results are shown in FIG. 1. In the figure, the symbol * indicates that a statistically significant difference was observed with respect to the TS-1 single administration group.

$$TV(mm^3)=(major\ axis \times minor\ axis^2)/2$$

$$T/C(\%)=(mean\ RTV\ value\ of\ test\ solution\ administration\ group)/(mean\ RTV\ value\ of\ control\ group) \times 100$$

Test Example 3

Enhancing Activity of Compounds of the Present Invention for Anti-Tumor Effect of TS-1

A human breast cancer cell line MX-1 was transplanted into the right-sided chest of each of 5- to 6-week-old male BALE/cA Jcl-nu mice, and used in the same manner as the Test Example 2.

Figure 2:
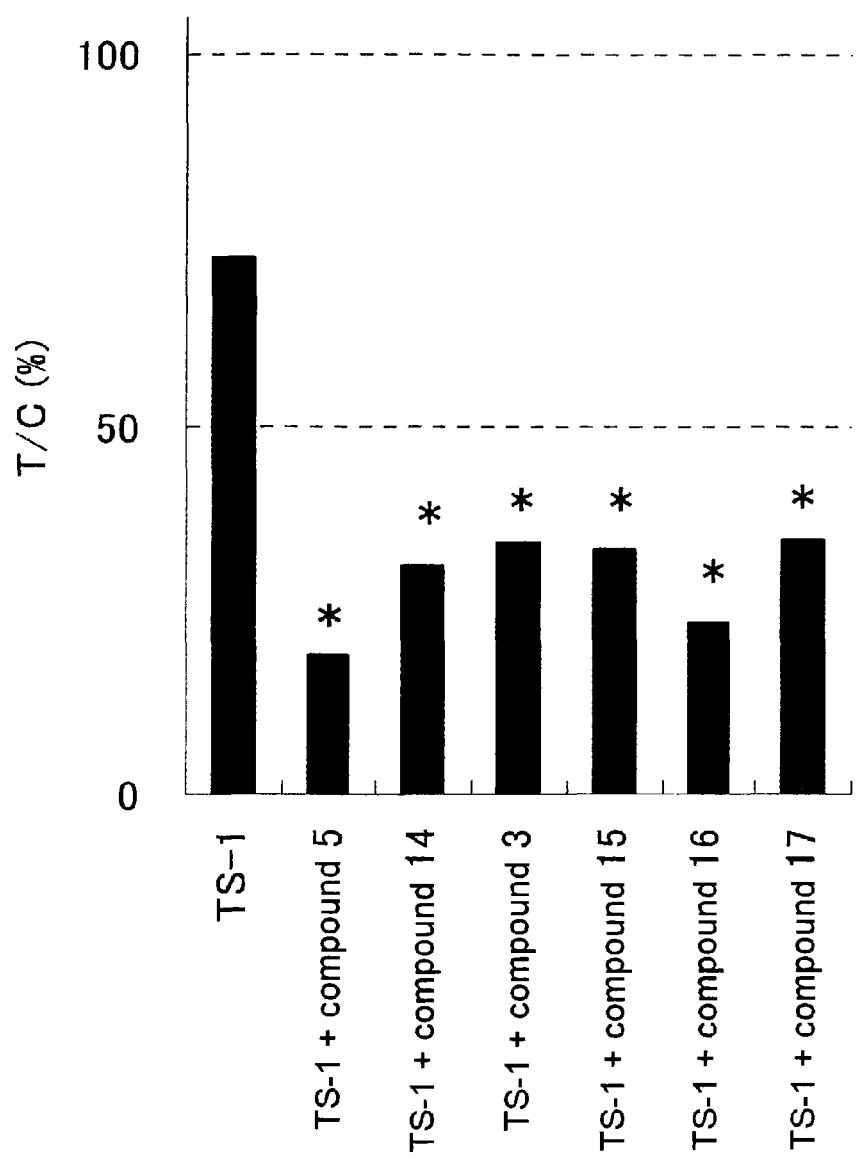
FIG. 2 is a diagram showing anti-tumor effect potentiating effect on TS-1.

A test solution for the TS-1 single administration group was prepared, in which the dose of TS-1 (10 mg/kg/day) was represented by the amount of FT. Test solutions for the combined administration group (TS-1+the compound of the present invention) were prepared, so as to be consisted by 300 mg/kg/day of the Compounds (5, 14, 3, 15, 16 and 17) of the present invention+TS-1 (10 mg/kg/day), and enhancing activity was evaluated in the same manner as in Test Example 2. The results are shown in FIG. 2. In the figure, the symbol * indicates that a statistically significant difference was observed with respect to the TS-1 single administration group.

Test Example 4

Enhancing Activity of Compounds of the Present Invention for Anti-Tumor Effect of 5-FU A human ovarian cancer cell line OVCAR-3 was transplanted into the right-sided chest of each of 5- to 6-week-old male BALB/cA Jcl-nu mice, and used in the same manner as in Test Example 2.

A test solution for the 5-FU single administration group was prepared by dissolving 5-FU in a 7% Meylon (pH 9.0) and the dose of 5-FU was adjusted to 15 mg/kg/day. A test solution containing the compound of the present invention was prepared by suspension in 0.5% hydroxypropyl methyl cellulose and the dose of the present compound is adjusted to 300 mg/kg/day.

Figure 3:
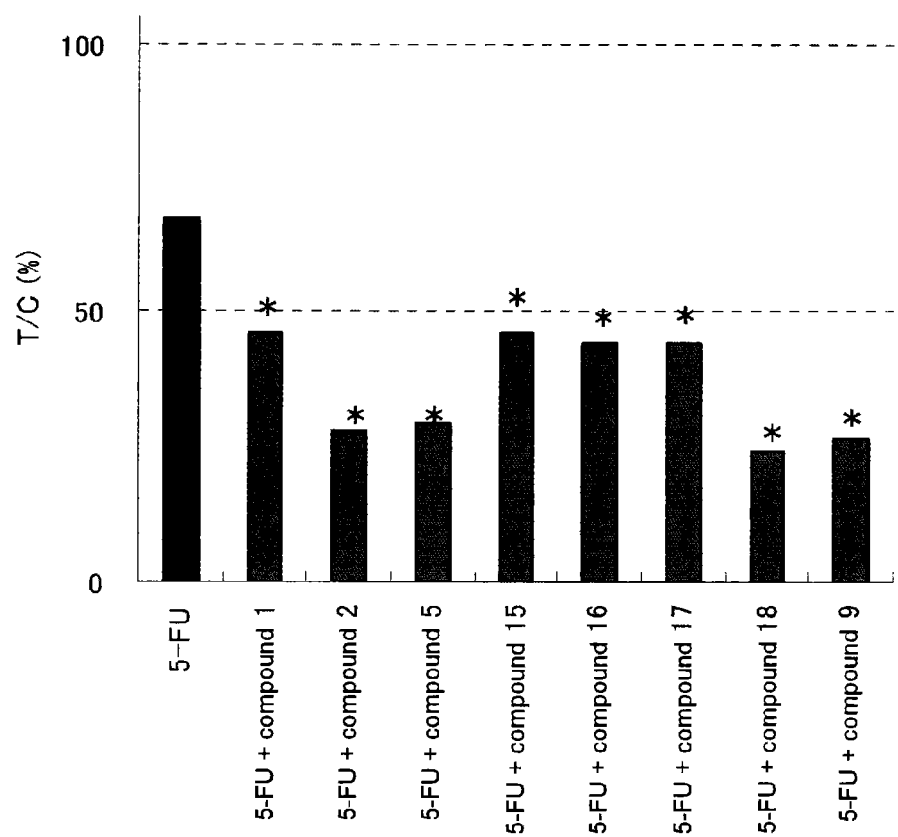
FIG. 3 is a diagram showing anti-tumor effect potentiating effect on 5-FU.

In the case of the 5-FU single administration group, the test solution was subcutaneously administered continuously for 14 days from day 1, using alzet osmotic mini-pump model 2002 (flow rate: 0.5 µl/h). In the case of the combined administration group (5-FU+the compound of the present invention), 5-FU was subcutaneously administered continuously for 14 days from day 1, using alzet osmotic mini-pump model 2002 (flow rate: 0.5 µl/h), and the test solution containing the compound of the present invention was orally administered to each mouse at 10 mL/kg volume of solution every day. Enhancing activity was evaluated in the same manner as in Test Example 2. The results are shown in FIG. 3. In the figure, the symbol * indicates that a statistically significant difference was observed with respect to the 5-FU single administration group.

Test Example 5

Enhancing Activity of Compounds of the Present Invention for Anti-Tumor Effect of Capecitabine A human breast cancer cell line MX-1 was transplanted into the right-sided chest of each of 5- to 6-week-old male BALB/cA Jcl-nu mice, and used in the same manner as in Test Example 2.

Figure 4:
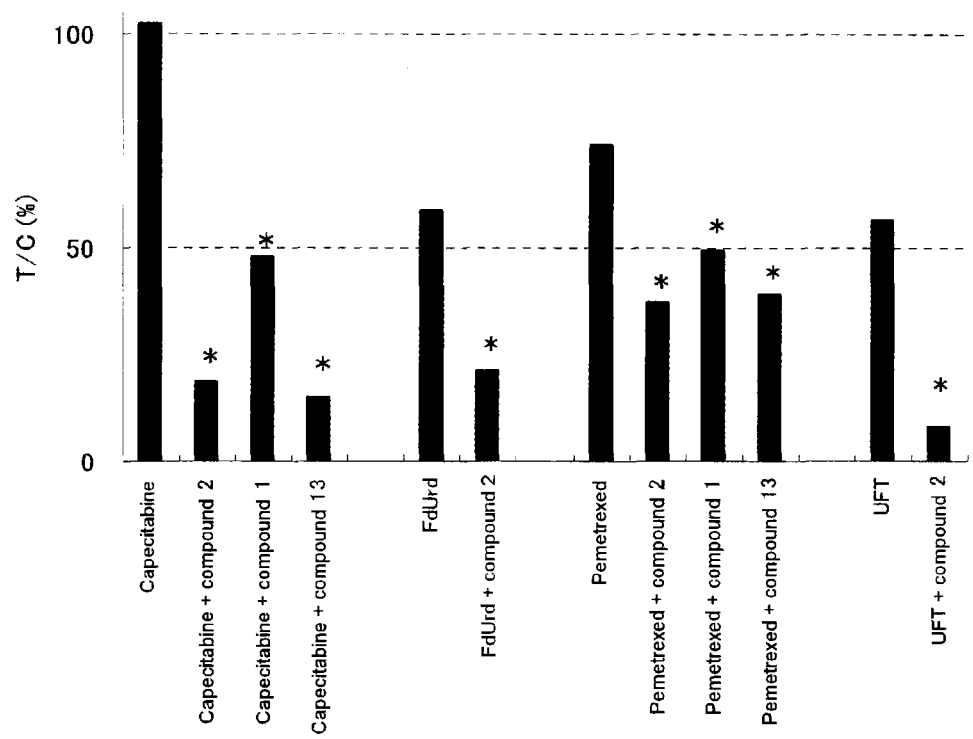
FIG. 4 is a diagram showing anti-tumor effect potentiating effect on capecitabine, FdUrd, pemetrexed and UFT.

A test solution for the capecitabine single administration group was prepared by suspending capecitabine in 0.5% hydroxypropyl methyl cellulose and the dose of the capecitabine was adjusted to 270 mg/kg/day. A test solution containing capecitabine and the compound of the present invention was prepared by suspending the two compounds in 0.5% hydroxypropyl methyl cellulose and the dose of the two compounds were adjusted to 300 mg/kg/day of the compound of the present invention and 270 mg/kg/day of capecitabine. Enhancing activity was evaluated out in the same manner as in Test Example 2. The results are shown in FIG. 4. In the figure, the symbol * indicates that a statistically significant difference was observed with respect to the capecitabine single administration group.

Test Example 6

Enhancing Activity of Compounds of the Present Invention for Anti-Tumor Effect of FdUrd A human breast cancer cell line MX-1 was transplanted into the right-sided chest of each of 5- to 6-week-old male BALB/cA Jcl-nu mice, and used in the same manner as in Test Example 2.

A test solution for the 5-fluoro-2'-deoxy-uridine (FdUrd) single administration group was prepared by dissolving FdUrd in a saline and the dose of the FdUrd was adjusted to 250 mg/kg/day. A test solution containing the compound of the present invention was prepared by suspending the present compound in 0.5% hydroxypropyl methyl cellulose and the dose of the present compound was adjusted to 300 mg/kg/day.

In the case of the FdUrd single administration group, the test solution was administered intravenously for 3 days from day 1. In the case of the combined administration group (FdUrd+the compound of the present invention), FdUrd was administered intravenously for 3 days from day 1, and the test solution containing the compound of the present invention was orally administered to each mouse at a dose of 10 mL/kg every day for 3 days from day 1. On day 15, enhancing activity was evaluated in the same manner as in Test Example 2. The results are shown in FIG. 4. In the figure, the symbol * indicates that a statistically significant difference was observed with respect to the FdUrd single administration group.

Test Example 7

Enhancing Activity of Compounds of the Present Invention for Anti-Tumor Effect of Pemetrexed A human breast cancer cell line MX-1 was transplanted into the right-sided chest of each of 5- to 6-week-old male BALB/cA Jcl-nu mice, and used in the same manner as in Test Example 2.

A test solution for the pemetrexed single administration group was prepared by dissolving pemetrexed in a saline and the dose of the pemetrexed was adjusted to 25 mg/kg/day. A test solution containing the compound of the present invention was prepared by suspending the present compound in 0.5% hydroxypropyl methyl cellulose and the dose of the present compound was adjusted to 300 mg/kg/day.

With regard to the pemetrexed single administration group, the test solution was administered intravenously on day 1 and day 8. With regard to the combined administration group (pemetrexed+the compound of the present invention), pemetrexed was administered intravenously on day 1 and day 8, and the test solution containing the compound of the present invention was orally administered to each mouse at 10 mL/kg volume of solution every day for 14 days from day 1. Enhancing activity was evaluated in the same manner as in Test Example 2. The results are shown in FIG. 4. In the figure, the symbol * indicates that a statistically significant difference was observed with respect to the pemetrexed single administration group.

Test Example 8

Enhancing Activity of Compounds of the Present Invention for Anti-Tumor Effect of UFT A human breast cancer cell line MX-1 was transplanted into the right-sided chest of each of 5- to 6-week-old male F344N Jcl-rnu rats, and used in the same manner as in Test Example 2.

A test solution for the tegafur/uracil (UFT, manufactured by Taiho Pharmaceutical Co., Ltd.) single administration group was prepared by suspending UFT in 0.5% hydroxypropyl methyl cellulose, the dose of UFT was 30 mg/kg/day which was represented by the amount of FT. A blended test solution containing UFT and the compound of the present invention was prepared by suspending the two compounds in 0.5% hydroxypropyl methyl cellulose and the dose of the two compounds is adjusted to 300 mg/kg/day of the compound of the present invention and 30 mg/kg/day of UFT.

With regard to the UFT single administration group, the test solution was orally administered every day for 21 days from day 1. With regard to the combined administration group (UFT+the compound of the present invention) as well, the test solution was orally administered every day for 21 days from day 1. On day 22, enhancing activity was evaluated in the same manner as in Test Example 2. The results are shown in FIG. 4. In the figure, the symbol * indicates that a statistically significant difference was observed with respect to the UFT single administration group.

Test Example 9

Toxicity and Efficacy of Compound of the Present Invention

For the purpose of safety assesment of the combined use of an anti-tumor agent with the compound of the present invention, the toxicity and anti-tumor effect when a high dose of the compound of the present invention was used in combination with the anti-tumor agent were evaluated.

A human stomach cancer cell line SC-6, a human colon cancer cell line LS174T, and a human pancreatic cancer cell line CFPAC-1 were transplanted into the right-sided chest of each of 5- to 6-week-old male BALB/cA Jcl-nu mice. After transplantation of each tumor, the major axis (mm) and minor axis (mm) of the tumor were measured, and the tumor volume (TV) was estimated by calculation. Using MiSTAT program, the mice were then divided into individual groups to adjust the mean TV of each group is to be equal. The date at which mice were divided into the group (n=5) was defined as day 0.

A test solution for the TS-1 single administration group was prepared using 0.5% hydroxypropyl methyl cellulose, and the dose of TS-1 was adjusted to 10 mg/kg/day as the amount of FT.

A test solution for the combined administration group (TS-1+the compound of the present invention) was prepared in the same manner as for the test solution for the single TS-1 administration group, so as to be consisted of the compound of the present invention (600 mg/kg/day)+TS-1 (10 mg/kg/day).

The test solution was orally administered to each mouse at 10 mL/kg volume of solution every day for 14 days from day 1.

In the toxicity, body weight change was measured over time. The mean body weight change rate [body weight change, BWC (%)] on day 15 to day 0 was calculated according to the following formula.

$$BWC(\%)=[(BW\ on\ Day\ 15)-(BW\ on\ Day\ 0)]/(BW\ on\ Day\ 0)\times 100$$

Figure 5:
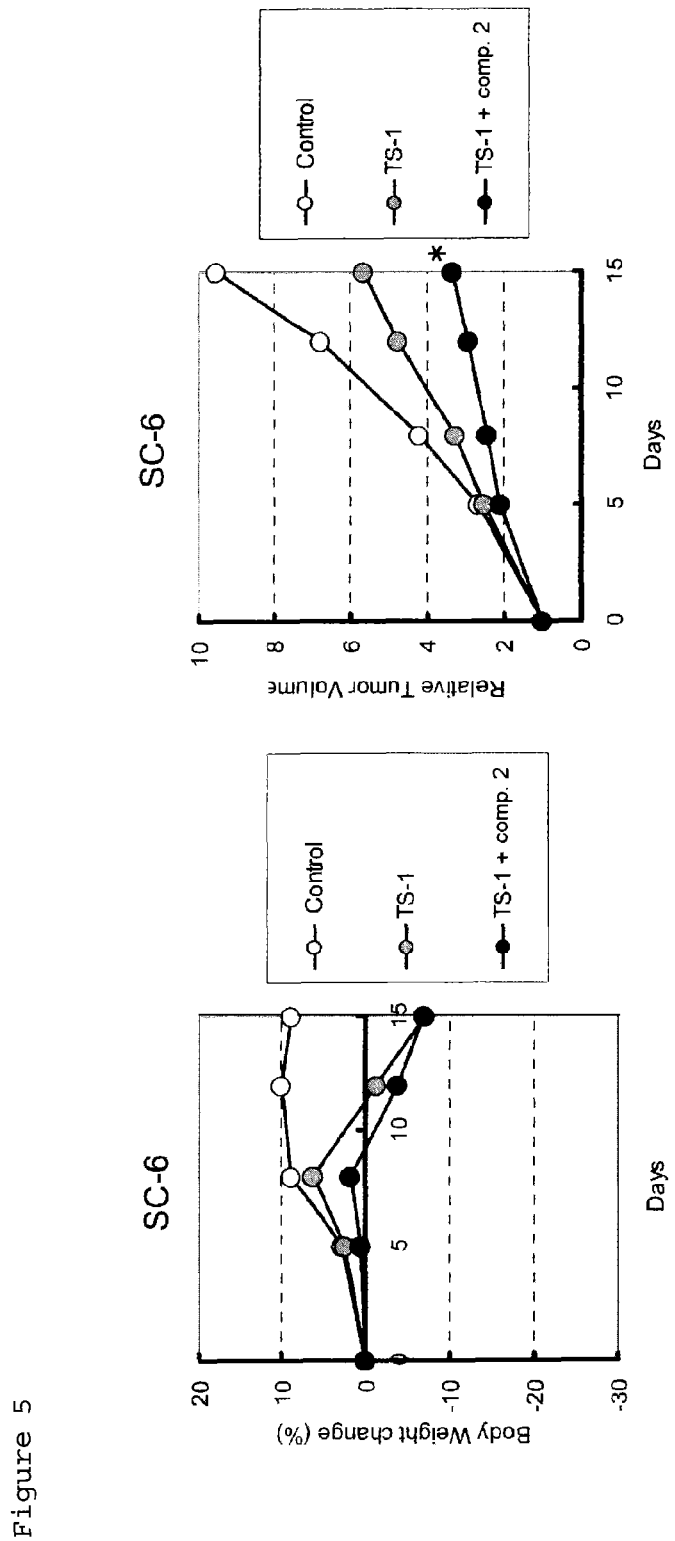
FIG. 5 is a diagram showing a body weight change and an anti-tumor effect in nude mice into which a human stomach cancer line SC-6 had been transplanted, in the case of administration of combination of the compound of the present invention and TS-1.
Figure 6:
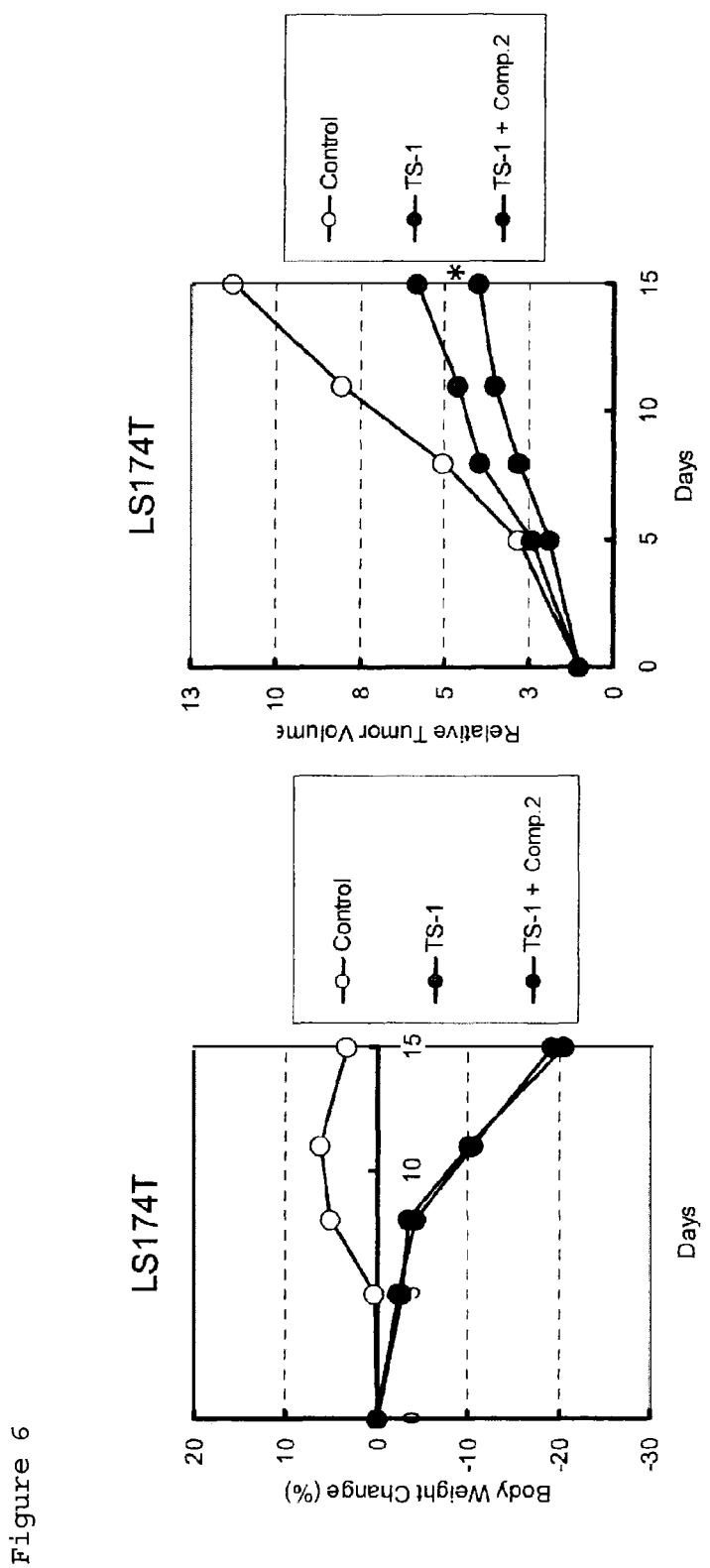
FIG. 6 is a diagram showing a body weight change and an anti-tumor effect in nude mice into which a human colon cancer line LS174T had been transplanted, in the case of administration of combination of the compound of the present invention and TS-1.
Figure 7:
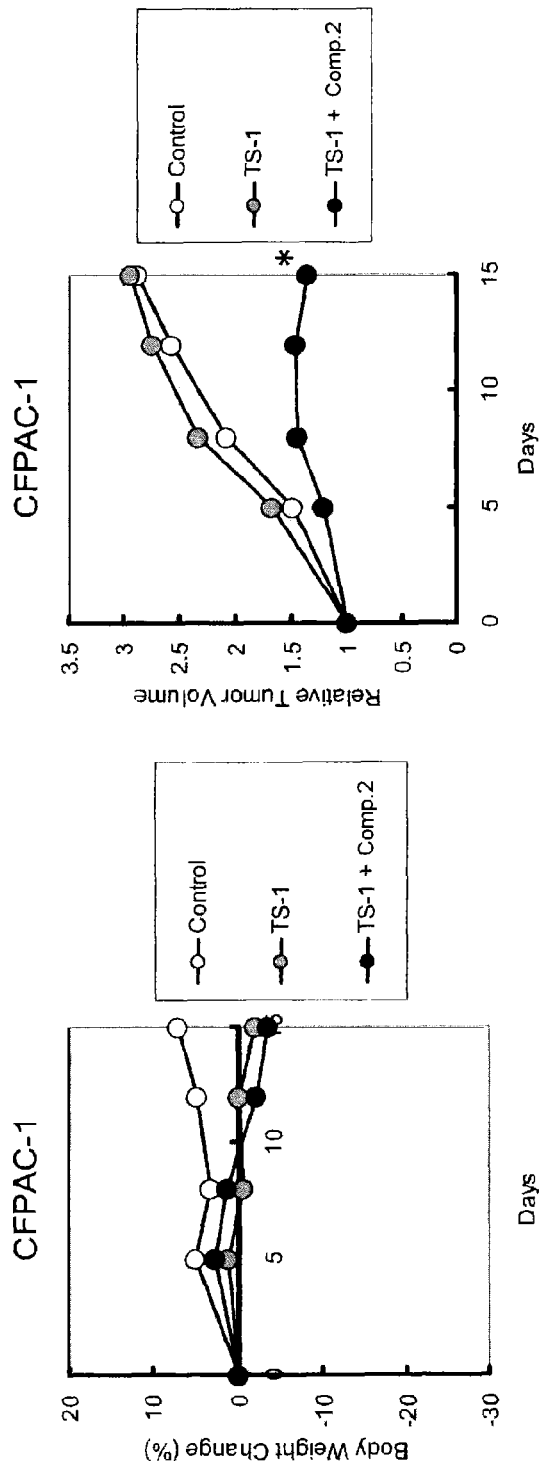
FIG. 7 is a diagram showing a body weight change and an anti-tumor effect in nude mice into which a human pancreatic cancer line CFPAC-1 had been transplanted, in the case of administration of combination of the compound of the present invention and TS-1.

In the case of anti-tumor effect, TV was measured, a relative tumor volume (RTV) to day 0 was calculated, and anti-tumor effect was evaluated. The results are shown in FIGS. 5 to 7. In the figures, the symbol * indicates that a statistically significant difference was observed with respect to the TS-1 single administration group.

$$TV(mm^3)=(major\ axis\times minor\ axis^2)/2$$

$$T/C(\%)=(mean\ RTV\ value\ of\ test\ solution\ administration\ group)/(mean\ RTV\ value\ of\ control\ group)\times 100$$

As shown in FIG. 1 to FIG. 4, the uracil compound of the formula (I) or a salt thereof has a significantly enhancing activity on the anti-tumor effects of anti-tumor agents, in particular, antimetabolites. On the other hand, as is shown in Table 10, although Comparative Compound 1 also has strong dUTPase inhibitory activity, enhancing activity was not observed. Moreover, as shown in FIG. 5 to FIG. 7, body weight loss in the case of the combined use of the uracil compound of the formula (I) or a salt thereof with an anti-tumor agent was not different from that in the case of single administration of anti-tumor agent, and thus, it was found that the uracil compound of the formula (I) or a salt thereof could enhance the anti-tumor effect of the anti-tumor agent without toxicity.

Test Example 10

Study 1 Regarding Molar Ratio of Combined Compounds Necessary for Enhancing Anti-Tumor Effects The combination ratio between the compound of the present invention and TS-1 necessary for achieving anti-tumor effect potentiating effect, when the two compounds are used in combination, was evaluated in mice.

A human breast cancer cell line MX-1 was transplanted into the right-sided chest of each of 5- to 6-week-old male BALB/cA Jcl-nu mice. After transplantation of the tumor, the major axis (mm) and minor axis (mm) of the tumor were measured, and the tumor volume (TV) was calculated. Using MiSTAT program, the mice were then divided into individual groups to adjust the mean TV of each group is to be equal. The date at which mice were divided into individual group (n=7) was defined as day 0.

The dose of TS-1 in a test solution for the TS-1 single administration group was adjusted to 8.3 mg/kg/day which is represented by the amount of FT. The dose of Compound 2 in a test solution for the Compound 2 single administration group was set at 1200 mg/kg/day. These test solutions were prepared using 0.5% hydroxypropyl methyl cellulose.

A test solution for the combined administration group (TS-1+the compound of the present invention) was prepared in the same manner as for the aforementioned test solution for the TS-1 single administration group, so as to be consisted of the compound of the present invention (1200, 600, 300 or 150 mg/kg/day)+TS-1 (8.3 mg/kg/day).

Figure 8:
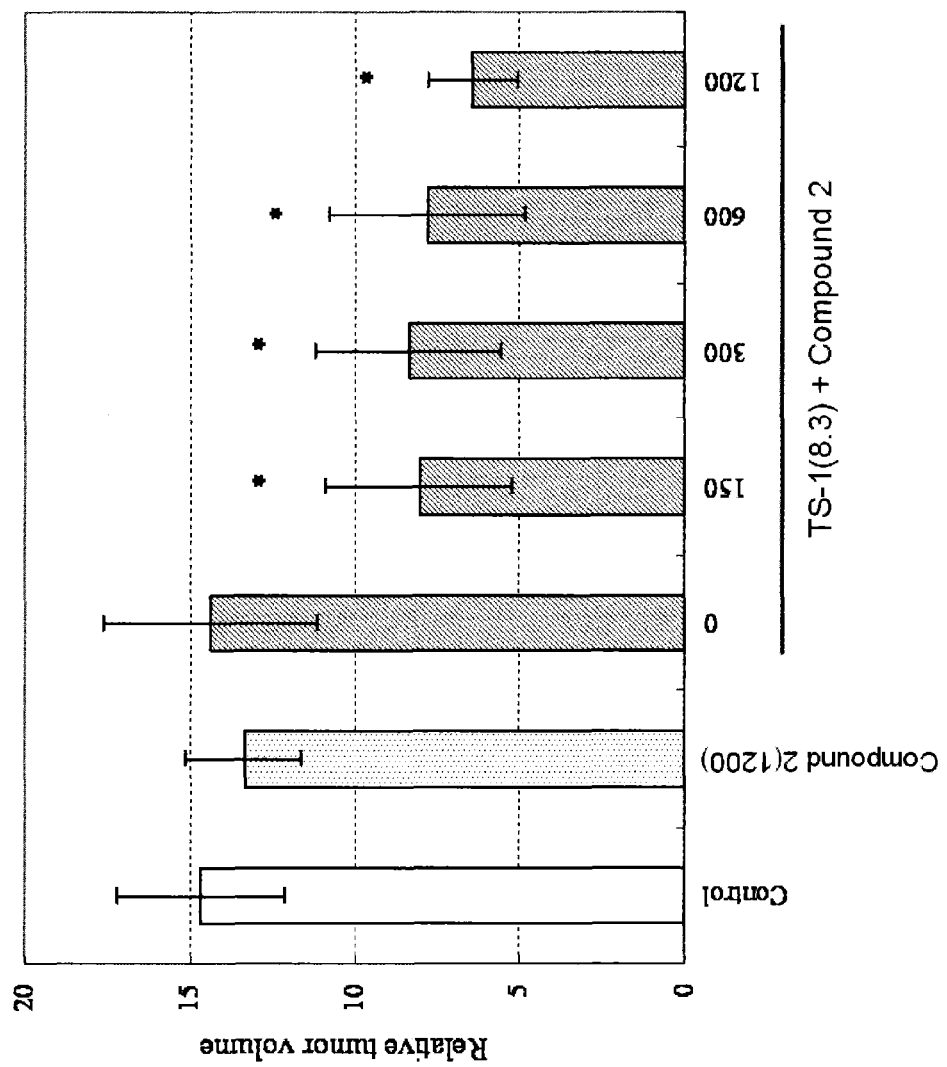
FIG. 8 is a diagram showing an anti-tumor effect in nude mice into which a human breast cancer line MX-1 had been transplanted, in the case of administration of combination of the compound of the present invention and TS-1.

Each test solution was orally administered to each mouse at 10 mL/kg volume of solution every day for 14 days from day 1, and enhancing activity was evaluated in the same manner as in Test Example 2. The results are shown in FIG. 8. In the figure, the symbol * indicates that a statistically significant difference was observed with respect to the TS-1 single administration group.

Test Example 11

Study 2 Regarding Molar Ratio of Combined Compounds Necessary for Enhancing Anti-Tumor Effects The combination ratio between the compound of the present invention and TS-1 necessary for achieving anti-tumor effect potentiating effect, when the two compounds are used in combination, was evaluated in rats.

A human breast cancer cell line MX-1 was transplanted into the right-sided chest of each of 5- to 6-week-old male F344N Jcl-rnu rats. After transplantation, the major axis (mm) and minor axis (mm) of the tumor were measured, and the tumor volume (TV) was calculated. Using MiSTAT program, the rats were then divided into individual groups to adjust the mean TV of each group is to be equal. The date at which rats were divided into individual group (n=5 or 6) was defined as day 0.

A test solution for the TS-1 single administration group was prepared using 0.5% hydroxypropyl methyl cellulose, in which the dose of TS-1 was adjusted to 18 mg/kg/day as the amount of FT.

A test solution containing for the combined administration group (TS-1+the compound of the present invention) was prepared in the same manner as for the aforementioned test solution for the TS-1 single administration group, so as to be consisted of the compound of the present invention (100, 50, 25, 12.5 or 6.25 mg/kg/day)+TS-1 (18 mg/kg/day).

Figure 9:
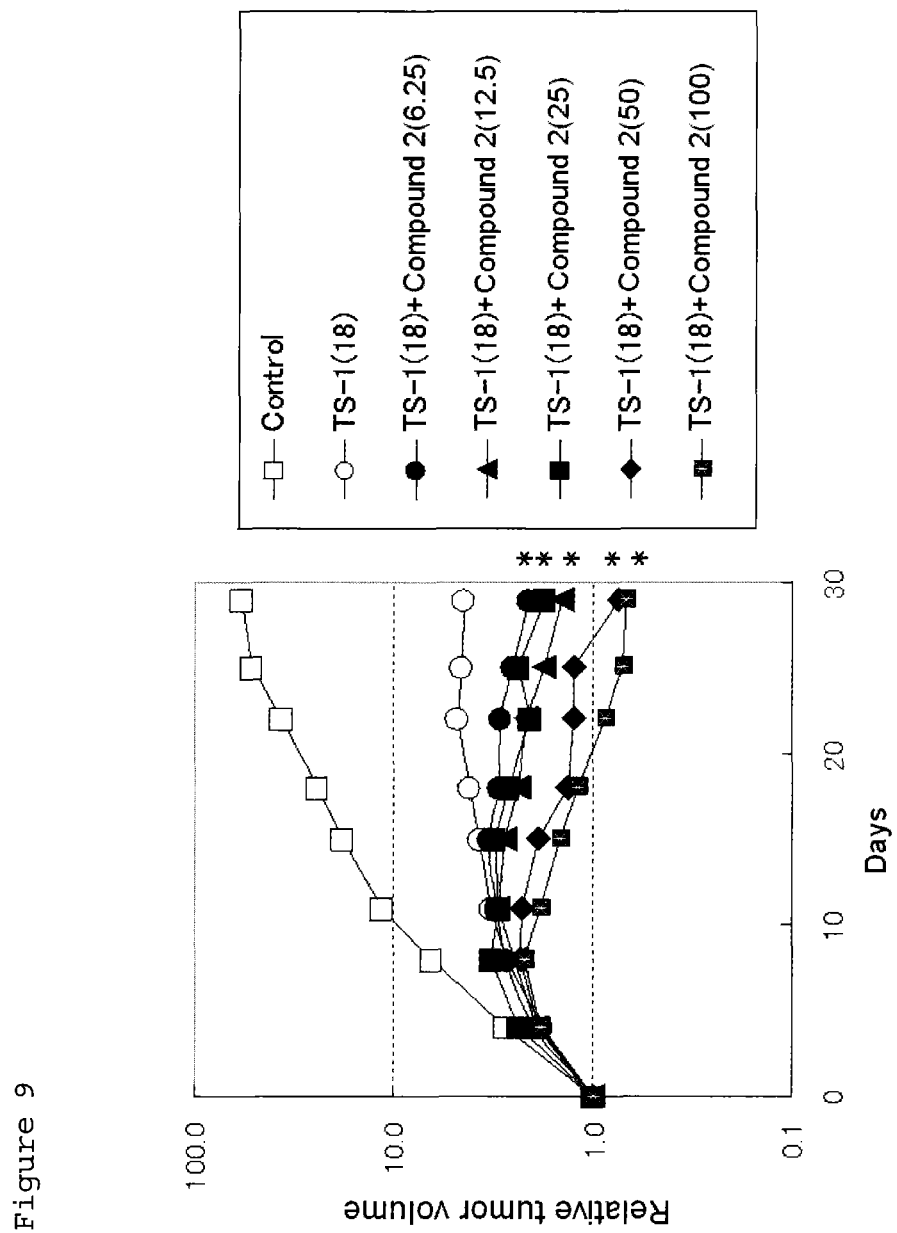
FIG. 9 is a diagram showing an anti-tumor effect in nude mice into which the human breast cancer line MX-1 had been transplanted, in the case of administration of combination of the compound of the present invention and TS-1.

Each test solution was orally administered to each rat at 10 mL/kg volume of solution every day for 28 days from day 1, and TV was measured on day 29. Enhancing activity was evaluated in the same manner as in Test Example 2. The results are shown in FIG. 9.

In the figure, the symbol * indicates that a statistically significant difference was observed with respect to the TS-1 single administration group.

Test Example 12

Study 3 Regarding Molar Ratio of Combined Compounds Necessary for Enhancing Anti-Tumor Effects The combination ratio between the compound of the present invention and capecitabine necessary for achieving anti-tumor effect potentiating effect, when the two compounds are used in combination, was evaluated in mice.

A human breast cancer cell line MX-1 was transplanted into the right-sided chest of each of 5- to 6-week-old male BALB/cA Jcl-nu mice. After transplantation, the major axis (mm) and minor axis (mm) of the tumor were measured, and the tumor volume (TV) was calculated. Using MiSTAT program, the mice were then divided into individual groups to adjust the mean TV of each group is to be equal. The date at which mice were divide into individual group (n =5) was defined as day 0.

A test solution for the capecitabine single administration group was prepared using 0.5% hydroxypropyl methyl cellulose to adjust the dose of capecitabine was set at 160, 359 or 809 mg/kg/day.

A test solution for the combined administration group (capecitabine+the compound of the present invention) was prepared in the same manner as for the aforementioned test solution for the capecitabine single administration group, so as to be consisted of the compound of the present invention (75, 300, 600, 1200 or 1600 mg/kg/day)+capecitabine (160, 359 or 809 mg/kg/day), as shown in the combination in the figure.

Figure 10:
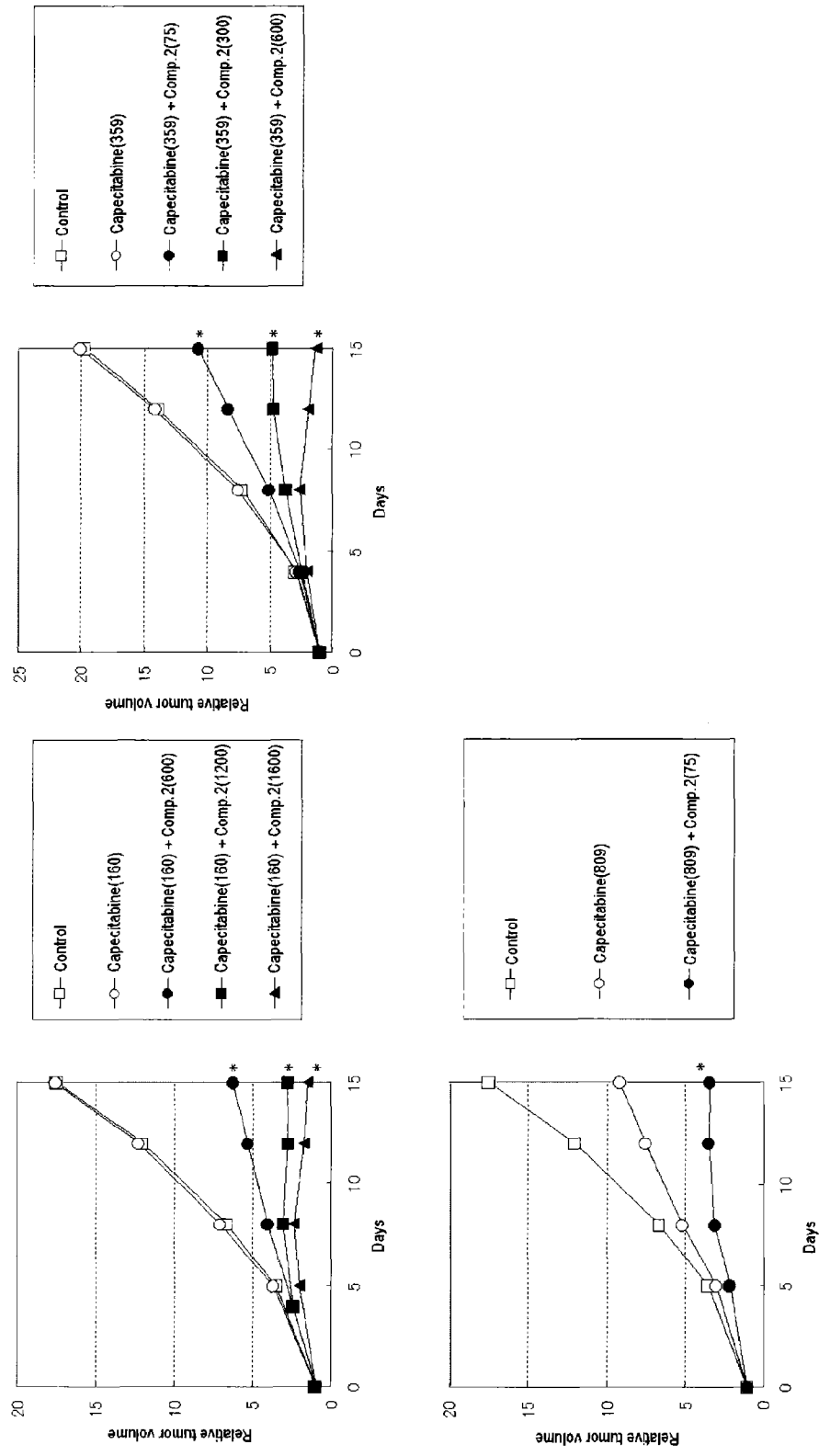
FIG. 10 is a diagram showing an anti-tumor effect in nude mice into which the human breast cancer line MX-1 had been transplanted, in the case of administration of combination of the compound of the present invention and capecitabine.

Each test solution was orally administered to each mouse at 10 mL/kg volume of solution every day for 14 day from day 1, and enhancing activity was evaluated in the same manner as in Test Example 2. The results are shown in FIG. 10. In the figure, the symbol * indicates that a statistically significant difference was observed with respect to the corresponding capecitabine single administration group.

The invention claimed is:

1. An anti-tumor drug, comprising an anti-tumor agent and a uracil compound represented by formula (I) or a pharmaceutically acceptable salt thereof:

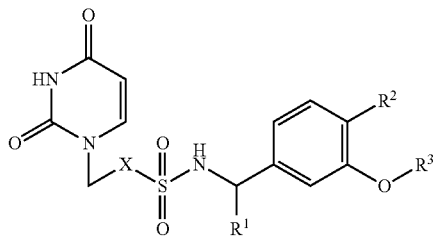

wherein:
X represents a $C_{1-5}$ alkylene group, such that one methylene group is optionally substituted with an oxygen atom;
$R^1$ represents a hydrogen atom or a $C_{1-6}$ alkyl group;
$R^2$ represents a hydrogen atom or a halogen atom;
$R^3$ represents a $C_{1-6}$ alkyl group, a $C_{2-6}$ alkenyl group, a $C_{3-6}$ cycloalkyl group, a ($C_{3-6}$ cycloalkyl) $C_{1-6}$ alkyl group, a halogeno-$C_{1-6}$ alkyl group or a saturated heterocyclic group; and
the anti-tumor agent is an antimetabolite.

2. The anti-tumor drug according to claim 1, wherein the antimetabolite is a thymidylate synthase inhibitor.

3. The anti-tumor drug according to claim 1, wherein the antimetabolite is at least one selected from the group consisting of 5-fluorouracil (5-FU), tegafur/gimeracil/oteracil potassium (TS-1), tegafur/uracil (UFT), capecitabine, 5-fluoro-2'-deoxy-uridine (FdUrd) and pemetrexed.

4. A method for potentiating an anti-tumor effect, the method comprising administering an effective amount of a uracil compound represented by formula (I) or a pharmaceutically acceptable salt thereof and an anti-tumor agent:

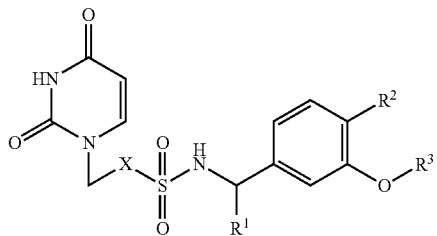

to a human in need thereof,
wherein:
X represents a $C_{1-5}$ alkylene group, such that one methylene group is optionally substituted with an oxygen atom;
$R^1$ represents a hydrogen atom or a $C_{1-6}$ alkyl group;
$R^2$ represents a hydrogen atom or a halogen atom; and
$R^3$ represents a $C_{1-6}$ alkyl group, a $C_{2-6}$ alkenyl group, a $C_{3-6}$ cycloalkyl group, a ($C_{3-6}$ cycloalkyl) $C_{1-6}$ alkyl group, a halogeno-$C_{1-6}$ alkyl group or a saturated heterocyclic group; and
the anti-tumor agent is an antimetabolite.

5. The method according to claim 4,
wherein:
X represents an ethylene group or an —O—$C_{1-4}$ alkylene group;
$R^1$ represents a hydrogen atom or a $C_{1-3}$ alkyl group; and
$R^2$ represents a hydrogen atom or a fluorine atom.

6. The method according to claim 4, wherein:
X represents an ethylene group or an —O—CH$_2$CH$_2$CH$_2$— group;
$R^1$ represents a hydrogen atom, a methyl group or an ethyl group;
$R^2$ represents a hydrogen atom or a fluorine atom; and
$R^3$ represents an isobutyl group, a 2-methylbutyl group, an allyl group, a cyclopentyl group, a cyclopropylmethyl group, a 2,2-difluoroethyl group, a 2,2,2-trifluoroethyl group, a tetrahydrofuryl group or a tetrahydropyryl group.

7. The method according to claim 4, wherein the compound of the formula (I) is selected from the group consisting of:
N-(3-(cyclopropylmethoxy)benzyl)-3-((2,4-dioxo-3,4-dihydropyrimidin-1(2H)-yl)methoxy)propane-1-sulfonamide;
(R)—N-(1-(3-(cyclopentyloxy)phenyl)ethyl)-3-((2,4-dioxo-3,4-dihydropyrimidin-1(2H)-yl)methoxy)propane-1-sulfonamide;
3-((2,4-dioxo-3,4-dihydropyrimidin-1(2H)-yl)methoxy)-N—((R)-1-(3-((R)-tetrahydrofuran-3-yloxy)phenyl)ethyl)propane-1-sulfonamide;
N-(3-(cyclopropylmethoxy)-4-fluorobenzyl)-3-((2,4-dioxo-3,4-dihydropyrimidin-1(2H)-yl)methoxy)propane-1-sulfonamide;
(R)—N-(1-(3-(cyclopropylmethoxy)-4-fluorophenyl)ethyl)-3-((2,4-dioxo-3,4-dihydropyrimidin-1(2H)-yl)methoxy)propane-1-sulfonamide;
N-(1-(3-(cyclopropylmethoxy)phenyl)ethyl)-3-((2,4-dioxo-3,4-dihydropyrimidin-1(2H)-yl)methoxy)propane-1-sulfonamide;
N-(3-(cyclopentyloxy)benzyl)-3-((2,4-dioxo-3,4-dihydropyrimidin-1(2H)-yl)methoxy)propane-1-sulfonamide;
(R)—N-(1-(3-(cyclopropylmethoxy)-4-fluorophenyl)propyl)-3-((2,4-dioxo-3,4-dihydropyrimidin-1(2H)-yl)methoxy)propane-1-sulfonamide;
(R)—N-(1-(3-(cyclopentyloxy)-4-fluorophenyl)ethyl)-3-((2,4-dioxo-3,4-dihydropyrimidin-1(2H)-yl)methoxy)propane-1-sulfonamide;
(R)-3-((2,4-dioxo-3,4-dihydropyrimidin-1(2H)-yl)methoxy)-N-(1-(3-(2,2,2-trifluoroethoxy)phenyl)ethyl)propane-1-sulfonamide;
(R)-3-((2,4-dioxo-3,4-dihydropyrimidin-1(2H)-yl)methoxy)-N-(1-(3-isobutoxyphenyl)ethyl)propane-1-sulfonamide;
3-((2,4-dioxo-3,4-dihydropyrimidin-1(2H)-yl)methoxy)-N—((R)-1-(3-((S)-2-methylbutoxy)phenyl)ethyl)propane-1-sulfonamide;
(R)—N-(1-(3-(2,2-difluoroethoxy)phenyl)ethyl)-3-((2,4-dioxo-3,4-dihydropyrimidin-1(2H)-yl)methoxy)propane-1-sulfonamide;
(R)-3-((2,4-dioxo-3,4-dihydropyrimidin-1(2H)-yl)methoxy)-N-(1-(3-(tetrahydro-2H-pyran-4-yloxy)phenyl)ethyl)propane-1-sulfonamide;
(R)-3-((2,4-dioxo-3,4-dihydropyrimidin-1(2H)-yl)methoxy)-N-(1-(4-fluoro-3-(2,2,2-trifluoroethoxy)phenyl)ethyl)propane-1-sulfonamide;
(R)—N-(1-(3-(2,2-difluoroethoxy)-4-fluorophenyl)ethyl)-3-((2,4-dioxo-3,4-dihydropyrimidin-1(2H)-yl)methoxy)propane-1-sulfonamide;
(R)—N-(1-(3-(allyloxy)phenyl)ethyl)-3-((2,4-dioxo-3,4-dihydropyrimidin-1(2H)-yl)methoxy)propane-1-sulfonamide;
(R)—N-(1-(3-(cyclopropylmethoxy)phenyl)ethyl)-3-((2,4-dioxo-3,4-dihydropyrimidin-1(2H)-yl)methoxy)propane-1-sulfonamide; and
(R)—N-(1-(3-(cyclopropylmethoxy)phenyl)propyl)-3-(2,4-dioxo-3,4-dihydropyrimidin-1(2H)-yl)propane-1-sulfonamide.

8. The method according to claim 4, wherein the antimetabolite is a thymidylate synthase inhibitor.

9. The method according to claim 4, wherein the antimetabolite is at least one selected from the group consisting of 5-fluorouracil (5-FU), tegafur/gimeracil/oteracil potassium (TS-1), tegafur/uracil (UFT), capecitabine, 5-fluoro-2'-deoxy-uridine (FdUrd) and pemetrexed.

10. The anti-tumor drug according to claim 1, wherein:
    X represents an ethylene group or an —O—$C_{1-4}$ alkylene group;
    $R^1$ represents a hydrogen atom or a $C_{1-3}$ alkyl group; and
    $R^2$ represents a hydrogen atom or a fluorine atom.

11. The anti-tumor drug according to claim 1, wherein:
    X represents an ethylene group or an —O—$CH_2CH_2CH_2$— group;
    $R^1$ represents a hydrogen atom, a methyl group or an ethyl group;
    $R^2$ represents a hydrogen atom or a fluorine atom; and
    $R^3$ represents an isobutyl group, a 2-methylbutyl group, an allyl group, a cyclopentyl group, a cyclopropylmethyl group, a 2,2-difluoroethyl group, a 2,2,2-trifluoroethyl group, a tetrahydrofuryl group or a tetrahydropyryl group.

12. The anti-tumor drug according to claim 1, wherein the compound of the formula (I) is selected from the group consisting of:
    N-(3-(cyclopropylmethoxy)benzyl)-3-((2,4-dioxo-3,4-dihydropyrimidin-1(2H)-yl)methoxy)propane-1-sulfonamide;
    (R)—N-(1-(3-(cyclopentyloxy)phenyl)ethyl)-3-((2,4-dioxo-3,4-dihydropyrimidin-1(2H)-yl)methoxy)propane-1-sulfonamide;
    3-((2,4-dioxo-3,4-dihydropyrimidin-1(2H)-yl)methoxy)-N—((R)-1-(3-((R)-tetrahydrofuran-3-yloxy)phenyl)ethyl)propane-1-sulfonamide;
    N-(3-(cyclopropylmethoxy)-4-fluorobenzyl)-3-((2,4-dioxo-3,4-dihydropyrimidin-1(2H)-yl)methoxy)propane-1-sulfonamide;
    (R)—N-(1-(3-(cyclopropylmethoxy)-4-fluorophenyl)ethyl)-3-((2,4-dioxo-3,4-dihydropyrimidin-1(2H)-yl)methoxy)propane-1-sulfonamide;
    N-(1-(3-(cyclopropylmethoxy)phenyl)ethyl)-3-((2,4-dioxo-3,4-dihydropyrimidin-1(2H)-yl)methoxy)propane-1-sulfonamide;
    N-(3-(cyclopentyloxy)benzyl)-3-((2,4-dioxo-3,4-dihydropyrimidin-1(2H)-yl)methoxy)propane-1-sulfonamide;
    (R)—N-(1-(3-(cyclopropylmethoxy)-4-fluorophenyl)propyl)-3-((2,4-dioxo-3,4-dihydropyrimidin-1(2H)-yl)methoxy)propane-1-sulfonamide;
    (R)—N-(1-(3-(cyclopentyloxy)-4-fluorophenyl)ethyl)-3-((2,4-dioxo-3,4-dihydropyrimidin-1(2H)-yl)methoxy)propane-1-sulfonamide;
    (R)-3-((2,4-dioxo-3,4-dihydropyrimidin-1(2H)-yl)methoxy)-N-(1-(3-(2,2,2-trifluoroethoxy)phenyl)ethyl)propane-1-sulfonamide;
    (R)-3-((2,4-dioxo-3,4-dihydropyrimidin-1(2H)-yl)methoxy)-N-(1-(3-isobutoxyphenyl)ethyl)propane-1-sulfonamide;
    3-((2,4-dioxo-3,4-dihydropyrimidin-1(2H)-yl)methoxy)-N—((R)-1-(3-((S)-2-methylbutoxy)phenyl)ethyl)propane-1-sulfonamide;
    (R)—N-(1-(3-(2,2-difluoroethoxy)phenyl)ethyl)-3-((2,4-dioxo-3,4-dihydropyrimidin-1(2H)-yl)methoxy)propane-1-sulfonamide;
    (R)-3-((2,4-dioxo-3,4-dihydropyrimidin-1(2H)-yl)methoxy)-N-(1-(3-(tetrahydro-2H-pyran-4-yloxy)phenyl)ethyl)propane-1-sulfonamide;
    (R)-3-((2,4-dioxo-3,4-dihydropyrimidin-1 (2H)-yl)methoxy)-N-(1-(4-fluoro-3-(2,2,2-trifluoroethoxy)phenyl)ethyl)propane-1-sulfonamide;
    (R)—N-(1-(3-(2,2-difluoroethoxy)-4-fluorophenyl)ethyl)-3-((2,4-dioxo-3,4-dihydropyrimidin-1(2H)-yl)methoxy)propane-1-sulfonamide;
    (R)—N-(1-(3-(allyloxy)phenyl)ethyl)-3-((2,4-dioxo-3,4-dihydropyrimidin-1(2H)-yl)methoxy)propane-1-sulfonamide;
    (R)—N-(1-(3-(cyclopropylmethoxy)phenyl)ethyl)-3-((2,4-dioxo-3,4-dihydropyrimidin-1(2H)-yl)methoxy)propane-1-sulfonamide; and
    (R)—N-(1-(3-(cyclopropylmethoxy)phenyl)propyl)-3-(2,4-dioxo-3,4-dihydropyrimidin-1(2H)-yl)propane-1-sulfonamide.

* * * * *